United States Patent
Kitchen et al.

(10) Patent No.: US 12,378,608 B2
(45) Date of Patent: Aug. 5, 2025

(54) METHODS FOR DEVELOPING URINE BIOMARKERS AND FOR DETECTING BLADDER CANCER

(71) Applicant: Exosome Diagnostics, Inc., Waltham, MA (US)

(72) Inventors: Robert Kitchen, Somerville, MA (US); Elena Castellanos-Rizaldos, Waltham, MA (US); Mia Sher, Maynard, MA (US); James Hurley, Marblehead, MA (US); Dalin Chan, Brighton, MA (US); Georg Stoll, Munich (DE); Wei Yu, Belmont, MA (US); Johan Skog, Lincoln, MA (US)

(73) Assignee: Exosome Diagnostics, Inc., Waltham, MA (US)

( * ) Notice: Subject to any disclaimer, the term of this patent is extended or adjusted under 35 U.S.C. 154(b) by 1148 days.

(21) Appl. No.: 15/734,363

(22) PCT Filed: Jun. 6, 2019

(86) PCT No.: PCT/US2019/035800
§ 371 (c)(1),
(2) Date: Dec. 2, 2020

(87) PCT Pub. No.: WO2019/236853
PCT Pub. Date: Dec. 12, 2019

(65) Prior Publication Data
US 2021/0230701 A1    Jul. 29, 2021

Related U.S. Application Data

(60) Provisional application No. 62/681,636, filed on Jun. 6, 2018.

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,812,023 B1 | 11/2004 | Lamparski et al. | |
| 6,899,863 B1 | 5/2005 | Dhellin et al. | |
| 7,198,923 B1 | 4/2007 | Abrignani et al. | |
| 7,998,695 B2 | 8/2011 | Nakamura et al. | |
| 2009/0175844 A1 | 7/2009 | Nakamura et al. | |
| 2011/0262921 A1 | 10/2011 | Sabichi et al. | |
| 2013/0172203 A1 | 7/2013 | Yeatman et al. | |
| 2015/0292030 A1 | 10/2015 | McConkey et al. | |

FOREIGN PATENT DOCUMENTS

| | | |
|---|---|---|
| WO | WO 2009/100029 A1 | 8/2009 |
| WO | WO 2014/107571 A1 | 7/2014 |
| WO | WO 2014/138396 A1 | 9/2014 |
| WO | WO 2016/007755 A1 | 1/2016 |
| WO | WO 2017/040520 A1 | 3/2017 |
| WO | WO 2017/214189 A1 | 12/2017 |
| WO | WO-2019236853 A1 | 12/2019 |

OTHER PUBLICATIONS

Enard et al. (Science 2002 vol. 296 p. 340) (Year: 2002).*
Al-Nedawi, K. et al., "Intercellular transfer of the oncogenic receptor EGFRvIII by microvesicles derived from tumour cells," Nat Cell Biol., 10:619-24 (2008).
Balzar, M. et al., "The biology of the 17-1A antigen (Ep-CAM)," J Mol Med., 77:699-712 (1999).
Blackwell, R. H. et al., "The untapped potential of urine shed bladder cancer exosomes: biomarkers, signaling, and therapeutics," Bladder, 1(1):e7 (2014); doi:10.14440/bladder.2014.38, 7 pages.
Biton, A. et al., "Independent Component Analysis Uncovers the Landscape of the Bladder Tumor Transcriptome and Reveals Insights into Luminal and Basal Subtypes," Cell Reports, 9:1235-1245 (2014).
Chen, C. et al., Microfluidic isolation and transcriptome analysis of serum microvesicles,' Lab Chip., 10(4):505-511 (2010).
Cheruvanky, A. et al., "Rapid isolation of urinary exosomal biomarkers using a nanomembrane ultrafiltration concentrator," Am J Physiol Renal Physiol, 292:F1657-F1661 (2007).
Miranda, K. C. et al., "Nucleic acids within urinary exosomes/microvesicles are potential biomarkers for renal disease," Kidney International , 78:191-199 (2010); doi:10.1038/ki.2010.106.
Nillson, J. et al., "Prostate cancer-derived urine exosomes: a novel approach to biomarkers for prostate cancer," British Journal of Cancer, 100:1603-1607 (2009).
Raposo, G. et al., "B Lymphocytes Secrete Antigen-presenting Vesicles," J. Exp. Med., 183:1161-1172 (1996).
Skog, J. et al., "Glioblastoma microvesicles transport RNA and protein that promote tumor growth and provide diagnostic biomarkers," Nat Cell Biol., 10(12):1470-1476 (2008).
Taylor, D. D. & Gercel-Taylor, C., "MicroRNA signatures of tumor-derived exosomes as diagnostic biomarkers of ovarian cancer," Gynecologic Oncology, 110:13-21 (2008).
Went, P. T. et al., "Frequent EpCam protein expression in human carcinomas," Hum Pathol., 35:122-128 (2004).

* cited by examiner

*Primary Examiner* — Katherine D Salmon
(74) *Attorney, Agent, or Firm* — Casimir Jones, S.C.; Peter J. Schlueter

(57) ABSTRACT

The present disclosure relates to methods for detecting and treating bladder cancer in a subject using the gene expression level measurements from exosomes derived from the subject.

19 Claims, 11 Drawing Sheets

| geneName | WT | Tumour | log2_FC_TumourOverWT | padj | Bladder_TPM | Bladder_Fraction | Urine_TPM | Urine_Fraction |
|---|---|---|---|---|---|---|---|---|
| DHRS2 | 1,86381 | 22380.3 | 0.26 | 0.75 | 61140 | 0.99 | 414.83 | 1 |
| UPK2 | 1730.2 | 7607.4 | 2.14 | 0.00 | 5568.6 | 0.99 | 94.1 | 1 |
| UPK1A | 5282.9 | 4216.5 | -0.33 | 0.72 | 17489.9 | 0.98 | 181.9 | 1 |
| KRT20 | 1142.6 | 3693.4 | 1.69 | 0.05 | 697.7 | 0.97 | 47.8 | 1 |
| UPK1B | 2668.1 | 7055.8 | 1.4 | 0.04 | 6111.9 | 0.95 | 15.2 | 1 |
| ACER2 | 974.9 | 847.1 | -0.2 | 0.74 | 3718.6 | 0.88 | 60 | 0.98 |
| SNX31 | 803.4 | 1364.9 | 0.76 | 0.32 | 2569.2 | 0.87 | 89.6 | 1 |
| VGLL1 | 442.9 | 1564.7 | 1.82 | 0.00 | 982.6 | 0.86 | 28.8 | 1 |
| FER1L4 | 1207.6 | 5053.4 | 2.07 | 0.00 | 13485.5 | 0.82 | 18.7 | 1 |
| UPK3A | 989 | 1464.9 | 0.57 | 0.51 | 4073.7 | 0.81 | 27.7 | 1 |
| OSR1 | 1175.4 | 510.5 | -1.2 | 0.01 | 9489.3 | 0.78 | 4.2 | 0.96 |
| GATA3 | 2750.1 | 5619.7 | 1.03 | 0.02 | 9844.6 | 0.65 | 172.4 | 0.99 |
| SCUBE2 | 2753.7 | 1591.6 | -0.79 | 0.21 | 7607.9 | 0.59 | 33.5 | 1 |
| GAPDH | 58291.9 | 90678.3 | 0.64 | 0.00 | 63710.8 | 0.31 | 170.8 | 0.58 |
| ADAM15 | 2832.3 | 4021.4 | 0.51 | 0.01 | 5963.4 | 0.27 | NA | NA |
| HBB | 1252.1 | 440.3 | -1.51 | 0.00 | 1020.9 | 0.02 | 0 | 0 |

FIG. 1

METHODS FOR DEVELOPING URINE BIOMARKERS AND FOR DETECTING BLADDER CANCER

CROSS-REFERENCE TO RELATED APPLICATIONS

This application is a U.S. National Phase Application, filed under 35 U.S.C. § 371, of International Application No. PCT/US2019/035800, filed on Jun. 6, 2019, which claims priority to, and the benefit of, U.S. Provisional Application No. 62/681,636, filed Jun. 6, 2018, the contents of each of which are incorporated herein by reference in their entireties.

BACKGROUND OF THE INVENTION

In molecular biology, molecules, such as nucleic acids, can be isolated from human sample material, such as plasma and other body fluids ('biofluids'), and further analyzed with a wide range of methodologies. Biofluids from humans (and other species) contain cells and cell-free sources of molecules shed by all cells of the body. Cell-free sources include extracellular vesicles ('EVs') and the molecules carried on or within ('EV cargo'; e.g. RNA, DNA, lipids, small metabolites, and proteins) and cell-free DNA (cfDNA), which is likely to be derived from apoptotic and necrotic tissue. EVs are membranous vesicles between 30 and 5,000 nm in diameter, the majority being 30-300 nm in diameter. EVs are also commonly referred to as exosomes and microvesicles. Exosomes are a class of EVs that are actively shed into the body by all living cells. They contain nucleic acids that derive directly from their source cells and have been isolated from multiple biofluids. As such, exosomes are a rich resource for liquid-biopsy based molecular diagnostics investigating the detection of genetic abnormalities associated with various diseases, including oncology.

Herein, we demonstrate the application of an exosome-based extraction and nucleic acid analysis method and workflow to liquid biopsy for patients suspected of carcinoma of the urinary bladder ('bladder cancer'). Bladder cancer is the thirteenth most common cause of cancer death worldwide and there are ~70,000 new cases diagnosed per year in the USA alone. The disease is three-fold more prevalent in men than in women, being the fourth most prevalent cancer in men.

There are distinct types of bladder cancer depending on how it is categorized. Several types of cancer can start in the bladder: urothelial carcinoma, also known as transitional cell carcinoma (TCC), is by far the most common type of bladder cancer accounting for about 90% cases. It starts in the urothelial cells that line the inside of the bladder. Urothelial cells also line other parts of the urinary tract, such as the part of the kidney that connects to the ureter, the ureters, and the urethra. Patients with bladder cancer sometimes have other tumors in these places, so the entire urinary tract needs to be checked for tumors. A bladder cancer is also often described based on how far it has invaded into the wall of the bladder: Non-invasive cancers are still in the inner layer of cells (the transitional epithelium) but have not grown into the deeper layers; Invasive cancers have grown into deeper layers of the bladder wall. These cancers are more likely to spread and are harder to treat. A bladder cancer can also be categorized as superficial or non-muscle invasive. These terms include both non-invasive tumors as well as any noninvasive tumors that have not grown into the main muscle layer of the bladder. Bladder cancers are also divided into two subtypes, papillary and flat, based on how they grow: Papillary carcinomas grow in slender, finger-like projections from the inner surface of the bladder toward the hollow center. Papillary tumors often grow toward the center of the bladder without growing into the deeper bladder layers. These tumors are called non-invasive papillary cancers. Very low-grade (slow growing), non-invasive papillary cancer is sometimes called papillary urothelial neoplasm of low-malignant potential (PUNLMP) and tends to have a very good outcome. On the other hand, flat carcinomas do not grow toward the hollow part of the bladder at all. If a flat tumor is only in the inner layer of bladder cells, it is known as a non-invasive flat carcinoma or a flat carcinoma in situ (CIS). If either a papillary or flat tumor grows into deeper layers of the bladder, it is called an invasive urothelial (or transitional cell) carcinoma.

One of the most frequent symptoms in a bladder cancer is the presence of blood in urine, either in the form of micro- or gross-hematuria. Hematuria is defined as three or more red blood cells per high-power microscope field (in a properly collected and centrifuged urine specimen) and is the definition that dictates which patients require further urologic evaluation. From those patients with visible blood in the urine, at the time of diagnosis around 40% will be at an advanced disease stage. On the other hand, hematuria can also be found in patients that have other non-malignant processes (i.e. cystitis, urinary tract infection, etc.). From the 10.8 million patients with hematuria that undergo urological examination in the USA, 35% will have cystoscopy either planned or performed. In addition to that, a substantial proportion of the CT scans that are routinely performed in the USA are done on asymptomatic patients with microhematuria. Because of this, distinguishing bladder cancer from other genitourinary abnormalities using a non-invasive test is highly desirable.

Presently, the most reliable method for detecting bladder cancer is cystoscopy followed by histology of biopsied lesions. However, this technique is time consuming, invasive with significant potential side effects, and its sensitivity is only approximately 90%, meaning that about 10 percent of cancers are not detected using these methods. Of the non-invasive methodologies, urine cytology, which detects exfoliated malignant cells microscopically, is the current preferred method. Although cytology has a specificity of about 95%, it has poor sensitivity (9-25%) for low-grade lesions, is extremely dependent on sample quality and suffers from high inter-observer variability.

Survival of cancer patients is greatly enhanced when the cancer is treated early. In the case of bladder cancer, patients diagnosed with early stage disease have 5-year survival rates of >90%, compared to approximately 15-30% for patients diagnosed with advanced disease. Therefore, developments that lead to early diagnosis of bladder cancer can lead to an improved prognosis for the patients. The established method for detecting bladder cancer using urine samples is cytology.

One drawback associated with urine testing is that individual biomarker levels can vary significantly with: (i) different urine collection methods (catheterized, voided, urine pellets); (ii) the diurnal timing of urine sampling; (iii) the point of sampling during voiding (e.g. midstream vs. end sample); (iv) urine concentration associated with varying fluid intake, kidney function or diseases that affect volume; and (v) the presence of blood in the urine, from visually undetectable microhematuria to gross hematuria. These variations have the potential to lead to false positive and false negative tests. Although some of this variation can be reduced using strict standard operating procedures, patient compliance with these procedures can be unreliable. The effect of varying urine concentration can, in some instances, be accounted for by assessing biomarker levels relative to urinary creatinine, however, this increases the cost and complexity of testing, particularly when sample preparation or storage methods differ for biomarker detection and creatinine measurement. The effect of blood, on the other hand, although could be crudely evaluated using a dipstick type of urinalysis paper, these tests by themselves do not confirm presence or absence of hematuria due to lack of sensitivity and specificity of the method; and an estimated 13% of asymptomatic individuals are present with red blood cells in the urine.

Thus, there is a need in the art for simple tools for the early detection and diagnosis of bladder cancer. A sample processing method robust to hematuria that could minimize or eliminate the effect of blood as interference substance, even from gross hematuria, on the test result would be highly desirable and useful for bladder cancer detection.

SUMMARY OF THE INVENTION

The present disclosure provides a method of identifying the presence or absence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject, wherein the biological sample comprises at least one microvesicular nucleic acid extracted from at least one microvesicle; determining at least one reference value in the biological sample; normalizing the expression level of the at least one gene to the at least one reference value to obtain a normalized expression level of the at least one gene; comparing the normalized expression level of the at least one gene to a predetermined cutoff value; and identifying the presence of bladder cancer in the subject when the normalized expression level of the at least one gene is greater than the predetermined cutoff value or identifying the absence of bladder cancer in the subject when the normalized expression level of the at least one gene is less than or equal to the predetermined cutoff value.

The present disclosure provides a method of identifying the presence or absence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject, wherein the biological sample comprises at least one microvesicular nucleic acid extracted from at least one microvesicle; determining at least one reference value in the biological sample; normalizing the expression level of the at least one gene to the at least one reference value to obtain a normalized expression level of the at least one gene; comparing the normalized expression level of the at least one gene to a predetermined cutoff value; and identifying the presence of bladder cancer in the subject when the normalized expression level of the at least one gene is less than the predetermined cutoff value or identifying the absence of bladder cancer in the subject when the normalized expression level of the at least one gene is greater than or equal to the predetermined cutoff value.

The present disclosure provides a method of identifying the presence or absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject, wherein the biological sample comprises at least one microvesicular nucleic acid extracted from at least one microvesicle; determining $\Delta_{expression}$, wherein $\Delta_{expression}$ is the difference between the expression level of the first gene and the expression level of the at least second gene; comparing $\Delta_{expression}$ to a predetermined cutoff value; identifying the presence of bladder cancer in the subject when $\Delta_{expression}$ is greater than the predetermined cutoff value or identifying the absence of bladder cancer in the subject when $\Delta_{expression}$ is less than or equal to the predetermined cutoff.

The present disclosure provides a method of identifying the presence or absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject, wherein the biological sample comprises at least one microvesicular nucleic acid extracted from at least one microvesicle; determining $\Delta_{expression}$, wherein $\Delta_{expression}$ is the difference between the expression level of the first gene and the expression level of the at least second gene; comparing $\Delta_{expression}$ to a predetermined cutoff value; and identifying the presence of bladder cancer in the subject when $\Delta_{expression}$ is less than the predetermined cutoff value or identifying the absence of bladder cancer in the subject when $\Delta_{expression}$ is greater than or equal to the predetermined cutoff.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject, wherein the biological sample comprises at least one microvesicular nucleic acid extracted from at least one microvesicle; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is greater than the second predetermined cutoff value or identifying the absence of bladder cancer in the subject when $\Delta_{expression}$ is less than or equal to the first predetermined cutoff value and the normalized expression level of the at least third gene is less than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject, wherein the biological sample comprises at least one microvesicular nucleic acid extracted from at least one microvesicle; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is less than the second predetermined cutoff value or identifying the absence of bladder cancer in the subject when $\Delta_{expression}$ is less than or equal to the first predetermined cutoff value and the normalized expression level of the at least third gene is greater than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject, wherein the biological sample comprises at least one microvesicular nucleic acid extracted from at least one microvesicle; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing expression to a first predetermined cutoff value; comparing the normalized expression level of the at least third gene to a second predetermined cutoff value; and identifying the presence of bladder cancer in the subject when expression is less than the first predetermined cutoff value and the normalized expression level of the at least third gene is greater than the second predetermined cutoff value or identifying the absence of bladder cancer in the subject when $\Delta_{expression}$ is greater than or equal to the first predetermined cutoff value and the normalized expression level of the at least third gene is less than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject, wherein the biological sample comprises at least one microvesicular nucleic acid extracted from at least one microvesicle; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is less than the first predetermined cutoff value and the normalized expression level of the at least third gene is less than the second predetermined cutoff value or identifying the absence of bladder cancer in the subject when $\Delta_{expression}$ is greater than or equal to the first predetermined cutoff value and the normalized expression level of the at least third gene is greater than or equal to the second predetermined cutoff value.

In methods of the present disclosure, an at least one gene can be UPK2. In methods of the present disclosure, a first gene can be UPK2, a second gene can be OSR1 and an at least third gene can be KRT20. In methods of the present disclosure, an at least one reference value is the expression level of at least one reference gene in the biological sample, the total concentration of cfDNA in a biological sample, the abundance of at least one DNA molecule in a biological sample, the abundance of at least one RNA molecule in the biological sample, the number of microvesicles in a biological sample, the abundance of at least one protein in the biological sample, the abundance of at least one metabolite in the biological sample or any combination thereof. In methods of the present disclosure, an at least one reference value can be the expression level of at least one reference gene in the biological sample. An at least one reference gene can DHRS2.

Bladder cancer can be recurrent bladder cancer. Bladder cancer can be relapsed bladder cancer.

In methods of the present disclosure, an at least one microvesicular nucleic acid can comprise microvesicular DNA, microvesicular RNA or a combination of microvesicular DNA and microvesicular RNA. An at least one microvesicular nucleic acid can comprise microvesicular RNA.

In methods of the present disclosure, an at least one microvesicle can be isolated from a bodily fluid sample from a subject. A bodily fluid sample can be filtered or pre-processed to remove cells, cellular debris or any combination thereof prior to the isolation of the at least one An at least one microvesicle can be isolated from the bodily fluid sample by a method comprising filtration, size exclusion chromatography, ion exchange chromatography, density gradient centrifugation, centrifugation, differential centrifugation, immunoabsorbent capture, affinity purification, affinity enrichment, affinity exclusion microfluidic separation, ultracentrifugation, nanomembrane ultrafiltration or any combination thereof. An at least one microvesicle can be isolated from the bodily fluid sample by contacting the bodily fluid sample with at least one affinity agent that binds to at least one surface marker present on the surface the at least one microvesicle. An at least one surface marker can be selected from ADAM10, CEACAM5, CEACAM6, EPCAM, ERBB2 (HER2), FZD2, ITGA3, ITGB4, MUC1, SDC1, SLC3A2, TFRC, TNFRSF4, TNFRSF12A and TNFSF10.

In methods of the present disclosure, a biological sample can further comprise at least one cell-free nucleic acid. An at least one cell-free nucleic acid can comprise cell-free DNA (cfDNA), cell-free RNA (cfRNA) or a combination of cfDNA and cfRNA.

In methods of the present disclosure, a biological sample can comprise cell-free DNA and microvesicular RNA. A biological sample can comprise microvesicular RNA.

In methods of the present disclosure, a biological sample can be a bodily fluid sample. A bodily fluid sample can comprise blood, plasma, serum, urine or any combination thereof. A bodily fluid sample can be filtered or processed to remove cells, cellular debris or any combination thereof.

A bodily fluid sample can comprise blood, plasma, serum, urine or any combination thereof. A bodily fluid sample comprises urine. Urine can comprise at least 0.05% blood, or at least 0.5% blood, or at least 1% blood or more than 1% blood.

A subject can have hematuria. Hematuria can be gross hematuria (macroscopic hematuria). Hematuria can be microscopic hematuria.

In methods of the present disclosure, a predetermined cutoff value can have a positive predictive value of at least 50%, or at least 60%, or at least 70%, or at least 80%, or at least 90%, or at least 95%, or at least 99%.

In methods of the present disclosure, a predetermined cutoff value can have a negative predictive value of at least 50%, or at least 60%, or at least 70%, or at least 80%, or at least 90%, or at least 95%, or at least 99%.

In methods of the present disclosure, a predetermined cutoff value can have a sensitivity of at least 50%, or at least 60%, or at least 70%, or at least 80%, or at least 90%, or at least 95%, or at least 99%.

In methods of the present disclosure, a predetermined cutoff value can have a specificity of at least 50%, or at least 60%, or at least 70%, or at least 80%, or at least 90%, or at least 95%, or at least 99%.

A subject can be at least 40 years of age. A subject can have previously had bladder cancer. A subject can have previously had a radical cystectomy. A subject can be suspected of having bladder cancer.

The methods of the present disclosure can further comprise administering to a subject having bladder cancer at least one therapeutically effective amount of at least one therapy. A therapy can comprise surgery, radiation therapy, chemotherapy, intravesical therapy, anti-cancer therapy, immunotherapy, intravesical immunotherapy, targeted-drug therapy, intravesical chemotherapy or any combination thereof. Surgery can comprise a radical cystectomy.

Methods of the present disclosure can further comprise providing a treatment recommendation for the subject. A treatment recommendation can comprise recommding further diagnostic tests, recommending the administration of at least one therapy or any combination thereof.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

FIG. 1 is a chart showing the 15 biomarkers and HBB used in the bladder cancer screening methods of the present disclosure.

DETAILED DESCRIPTION OF THE INVENTION

Figure 2:
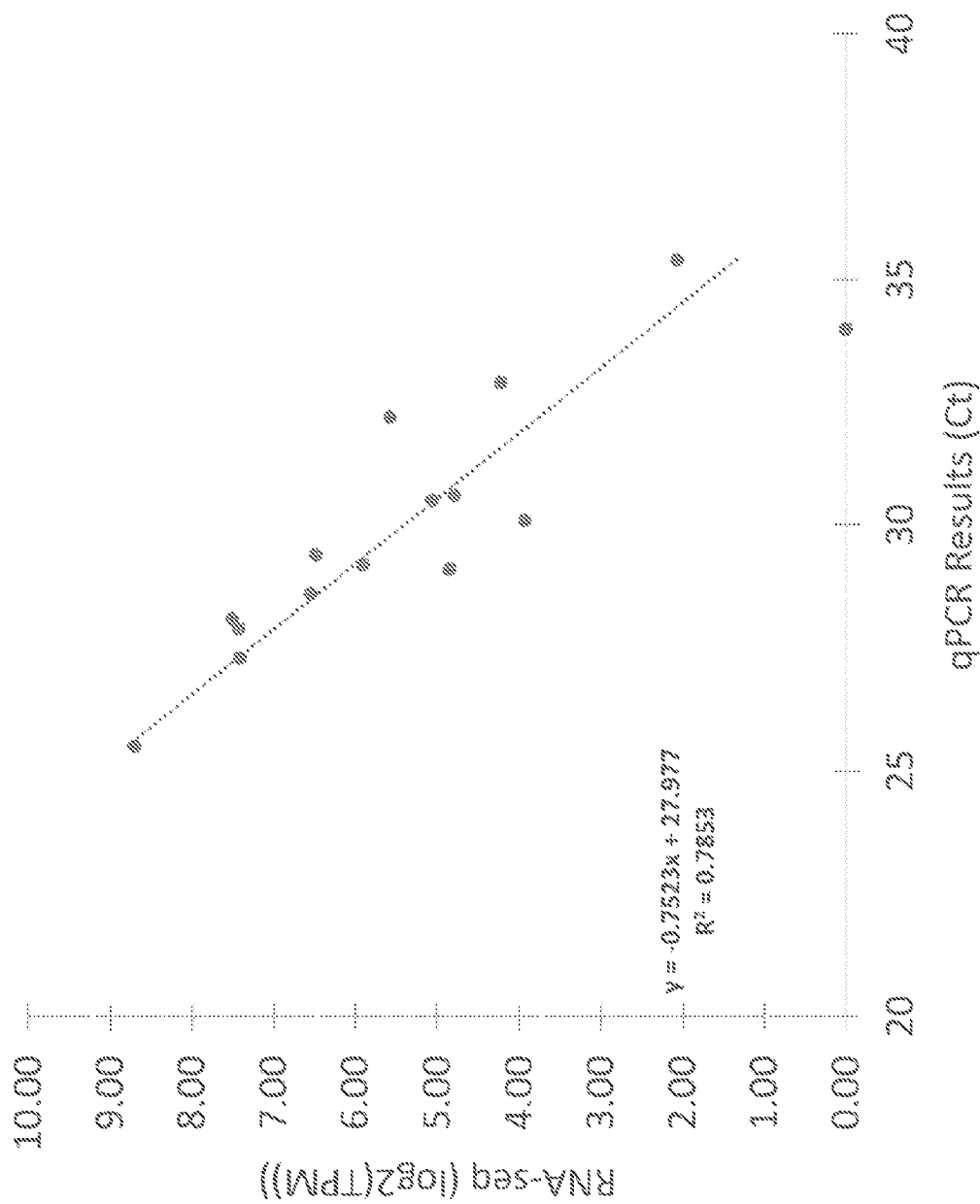
FIG. 2 is a graph showing a comparison of expression levels of the 15 biomarkers of the present disclosure measured using either RNA-seq analysis (y-axis) or qPCR analysis (x-axis).

The present disclosure provides methods for providing a clinical assessment of a subject in need therefore. The clinical assessment can include, but is not limited to, diagnosing a subject, monitoring a subject, recommending a treatment for a subject or prognosing a subject. In some aspects, the clinical assessment is informed by the analysis of the contents of microvesicles.

Microvesicles are shed by eukaryotic and prokaryotic cells, or budded off of the plasma membrane, to the exterior of the cell. These membrane vesicles are heterogeneous in size with diameters ranging from about 10 nm to about 5000 nm. All membrane vesicles shed by cells<0.8 µm in diameter are referred to herein collectively as "exosomes", "extracellular vesicles", or "microvesicles." These extracellular vesicles (EVs) include microvesicles, microvesicle-like particles, prostasomes, dexosomes, texosomes, ectosomes, oncosomes, apoptotic bodies, retrovirus-like particles, and human endogenous retrovirus (HERV) particles. Small microvesicles (approximately 10 to 1000 nm, and more often 30 to 200 nm in diameter) that are released by exocytosis of intracellular multivesicular bodies are referred to in the art as "microvesicles". Microvesicles shed by cells are also herein referred to as "exosomes". The terms extracellular vesicles, vesicles, microvesicles and exosomes are used interchangeably herein.

Exosomes are known to contain nucleic acids, including various DNA and RNA types such as mRNA (messenger RNA), miRNA (micro RNA), tRNA (transfer RNA), piRNA (piwi-interacting RNA), snRNA (small nuclear RNA), snoRNA (small nucleolar RNA), and rRNA (ribosomal RNA), various classes of long non-coding RNA, including long intergenic non-coding RNA (lincRNA) as well as proteins. Recent studies reveal that nucleic acids within microvesicles have a role as biomarkers. For example, WO 2009/100029 describes, among other things, the use of nucleic acids extracted from microvesicles in Glioblastoma multiforme (GBM, a particularly aggressive form of cancer) patient serum for medical diagnosis, prognosis and therapy evaluation. WO 2009/100029 also describes the use of nucleic acids extracted from microvesicles in human urine for the same purposes. The use of nucleic acids extracted from microvesicles is considered to potentially circumvent the need for biopsies, highlighting the enormous diagnostic potential of microvesicle biology (Skog et al. *Nature Cell Biology*, 2008, 10 (12): 1470-1476.

Microvesicles can be isolated from liquid biopsy samples from a subject, involving biofluids such as whole blood, serum, plasma, urine, and cerebrospinal fluid (CSF). The nucleic acids contained within the microvesicles can subsequently be extracted. The extracted nucleic acids, e.g., exosomal RNA, also referred to herein as "exoRNA," can be further analyzed based on detection of a biomarker or a combination of biomarkers. The analysis can be used to generate a clinical assessment that diagnoses a subject with a disease, predicts the disease outcome of the subject, stratifies the subject within a larger population of subjects, predicts whether the subject will respond to a particular therapy, or determines if a subject is responding to an administered therapy.

Various methods of the present disclosure are described in full detail herein.

The present disclosure provides a method of identifying the presence or absence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least one gene to the expression level of the at least one reference gene to obtain a normalized expression level of the at least one gene; comparing the normalized expression level of the at least one gene to a predetermined cutoff value; and identifying the presence of bladder cancer in the subject when the normalized expression level of the at least one gene is greater than the predetermined cutoff value or identifying the absence of bladder cancer in the subject when the normalized expression level of the at least one gene is less than or equal to the predetermined cutoff value.

The present disclosure provides a method of treating bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least one gene to the expression level of the at least one reference gene to obtain a normalized expression level of the at least one gene; comparing the normalized expression level of the at least one gene to a predetermined cutoff value; and administering to the subject at least one therapeutically effective amount of at least one first therapy when the normalized expression level of the at least one gene is greater than the predetermined cutoff value.

The present disclosure provides a method of identifying the presence or absence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least one gene to the expression level of the at least one reference gene to obtain a normalized expression level of the at least one gene; comparing the normalized expression level of the at least one gene to a predetermined cutoff value; and identifying the presence of bladder cancer in the subject when the normalized expression level of the at least one gene is less than the predetermined cutoff value or identifying the absence of bladder cancer in the subject when the normalized expression level of the at least one gene is greater than or equal to the predetermined cutoff value.

The present disclosure provides a method of treating bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least one gene to the expression level of the at least one reference gene to obtain a normalized expression level of the at least one gene; comparing the normalized expression level of the at least one gene to a predetermined cutoff value; and administering to the subject at least one therapeutically effective amount of at least one first therapy when the normalized expression level of the at least one gene is less than the predetermined cutoff value.

The present disclosure provides a method of identifying the presence or absence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least one gene to the at least one reference value to obtain a normalized expression level of the at least one gene; comparing the normalized expression level of the at least one gene to a predetermined cutoff value; and identifying the presence of bladder cancer in the subject when the normalized expression level of the at least one gene is greater than the predetermined cutoff value or identifying the absence of bladder cancer in the subject when the normalized expression level of the at least one gene is less than or equal to the predetermined cutoff value.

The present disclosure provides a method of treating bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least one gene to the at least one reference value to obtain a normalized expression level of the at least one gene; comparing the normalized expression level of the at least one gene to a predetermined cutoff value; and administering to the subject at least one therapeutically effective amount of at least one first therapy when the normalized expression level of the at least one gene is greater than the predetermined cutoff value.

The present disclosure provides a method of identifying the presence or absence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least one gene to the at least one reference value to obtain a normalized expression level of the at least one gene; comparing the normalized expression level of the at least one gene to a predetermined cutoff value; and identifying the presence of bladder cancer in the subject when the normalized expression level of the at least one gene is less than the predetermined cutoff value or identifying the absence of bladder cancer in the subject when the normalized expression level of the at least one gene is greater than or equal to the predetermined cutoff value.

The present disclosure provides a method of treating bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least one gene to the at least one reference value to obtain a normalized expression level of the at least one gene; comparing the normalized expression level of the at least one gene to a predetermined cutoff value; and administering to the subject at least one therapeutically effective amount of at least one first therapy when the normalized expression level of the at least one gene is less than the predetermined cutoff value.

The present disclosure provides a method of determining the risk of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least one gene to the expression level of the at least one reference gene to obtain a normalized expression level of the at least one gene; determining the risk of bladder cancer in the subject based on the normalized expression level of the at least one gene.

The present disclosure provides a method of determining the risk of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least one gene to the at least one reference value to obtain a normalized expression level of the at least one gene; determining the risk of bladder cancer in the subject based on the normalized expression level of the at least one gene.

In some aspects, any of the preceding methods can comprise determining the expression of at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB.

The present disclosure provides a method for identifying the presence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least one gene to the expression level of the at least one reference gene to obtain a normalized expression level of the at least one gene; and comparing the normalized expression level of the at least one gene to a predetermined cutoff value.

The present disclosure provides a method for identifying the presence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least one gene to the at least one reference value to obtain a normalized expression level of the at least one gene; and comparing the normalized expression level of the at least one gene to a predetermined cutoff value.

In some aspects, the preceding methods can further comprise identifying the presence of bladder cancer in the subject when the normalized expression level of the at least one gene is greater than the predetermined cutoff value. In some aspects, the preceding method can further comprise identifying the presence of bladder cancer in the subject when the normalized expression level of the at least one gene is greater than or equal to the predetermined cutoff value. In some aspects, the preceding method can further comprise identifying the presence of bladder cancer in the subject when the normalized expression level of the at least one gene is less than the predetermined cutoff value. In some aspects, the preceding method can further comprise identifying the presence of bladder cancer in the subject when the normalized expression level of the at least one gene is less than or equal to the predetermined cutoff value.

In some aspects, the preceding methods can comprise determining the expression of at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB.

The present disclosure provides a method for treating bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least one gene to the expression level of the at least one reference gene to obtain a normalized expression level of the at least one gene; and comparing the normalized expression level of the at least one gene to a predetermined cutoff value.

The present disclosure provides a method for treating bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least one gene to the at least one reference value to obtain a normalized expression level of the at least one gene; and comparing the normalized expression level of the at least one gene to a predetermined cutoff value.

In some aspects, the preceding methods can further comprise administering to the subject at least one therapeutically effective amount of at least one first therapy when the normalized expression level of the at least one gene is greater than the predetermined cutoff value. In some aspects, the preceding method can further comprise administering to the subject at least one therapeutically effective amount of at least one first therapy when the normalized expression level of the at least one gene is greater than or equal to the predetermined cutoff value. In some aspects, the preceding method can further comprise administering to the subject at least one therapeutically effective amount of at least one first therapy when the normalized expression level of the at least one gene is less than the predetermined cutoff value. In some aspects, the preceding method can further comprise administering to the subject at least one therapeutically effective amount of at least one first therapy when the normalized expression level of the at least one gene is less than or equal to the predetermined cutoff value.

In some aspects, the preceding methods can comprise determining the expression of at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB.

In some aspects of the preceding methods, the at least one gene can be UPK2 and the at least one reference gene can be DHRS2. Thus, the present disclosure provides a method for identifying the presence of bladder cancer in a subject comprising: determining the expression level of UPK2 and the expression level the reference gene DHRS2 in a biological sample from the subject; normalizing the expression level of UPK2 to the expression level of DHRS2 to obtain a normalized expression level of UPK2; and comparing the normalized expression level of UPK2 to a predetermined cutoff value; and identifying the presence of bladder cancer in the subject when the normalized expression level of UPK2 is less than the predetermined cutoff value. The present disclosure also provides a method for treating bladder cancer in a subject comprising determining the expression level of UPK2 and the expression level the reference gene DHRS2 in a biological sample from the subject; normalizing the expression level of UPK2 to the expression level of DHRS2 to obtain a normalized expression level of UPK2; and comparing the normalized expression level of UPK2 to a predetermined cutoff value; and administering at least one therapeutically effective dose of at least one first therapy to the subject when the normalized expression level of UPK2 is less than the predetermined cutoff value.

The present disclosure provides a method for identifying the absence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least one gene to the expression level of the at least one reference gene to obtain a normalized expression level of the at least one gene; and comparing the normalized expression level of the at least one gene to a predetermined cutoff value.

The present disclosure provides a method for identifying the absence of bladder cancer in a subject comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least one gene to the at least one reference value to obtain a normalized expression level of the at least one gene; and comparing the normalized expression level of the at least one gene to a predetermined cutoff value.

In some aspects, the preceding methods can further comprise identifying the absence of bladder cancer in the subject when the normalized expression level of the at least one gene is greater than the predetermined cutoff value. In some aspects, the preceding method can further comprise identifying the absence of bladder cancer in the subject when the normalized expression level of the at least one gene is greater than or equal to the predetermined cutoff value. In some aspects, the preceding method can further comprise identifying the absence of bladder cancer in the subject when the normalized expression level of the at least one gene is less than the predetermined cutoff value. In some aspects, the preceding method can further comprise identifying the absence of bladder cancer in the subject when the normalized expression level of the at least one gene is less than or equal to the predetermined cutoff value.

In some aspects, the preceding methods can comprise determining the expression of at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB.

The present disclosure provides a method of identifying the presence or absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the at least second gene to the expression level of the at least one reference gene to obtain a normalized expression level of the at least second gene; determining $\Delta_{expression}$, wherein $\Delta_{expression}$ is the difference between the normalized expression level of the first gene and the normalized expression level of the at least second gene; comparing $\Delta_{expression}$ to a predetermined cutoff value; and identifying the presence of bladder cancer in the subject when $\Delta_{expression}$ is greater than the predetermined cutoff value or identifying the absence of bladder cancer in the subject when $\Delta_{expression}$ is less than or equal to the predetermined cutoff.

The present disclosure provides a method of identifying the presence or absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the at least second gene to the at least one reference value to obtain a normalized expression level of the at least second gene; determining $\Delta_{expression}$, wherein $\Delta_{expression}$ is the difference between the normalized expression level of the first gene and the normalized expression level of the at least second gene; comparing $\Delta_{expression}$ to a predetermined cutoff value; and identifying the presence of bladder cancer in the subject when $\Delta_{expression}$ is greater than the predetermined cutoff value or identifying the absence of bladder cancer in the subject when $\Delta_{expression}$ is less than or equal to the predetermined cutoff.

The present disclosure provides a method of identifying the presence or absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining $\Delta_{expression}$, wherein $\Delta_{expression}$ is the difference between the expression level of the first gene and the expression level of the at least second gene; comparing $\Delta_{expression}$ to a predetermined cutoff value; and identifying the presence of bladder cancer in the subject when $\Delta_{expression}$ is greater than the predetermined cutoff value or identifying the absence of bladder cancer in the subject when $\Delta_{expression}$ is less than or equal to the predetermined cutoff.

The present disclosure provides a method of treating bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the at least second gene to the expression level of the at least one reference gene to obtain a normalized expression level of the at least second gene; determining $\Delta_{expression}$, wherein $\Delta_{expression}$ is the difference between the normalized expression level of the first gene and the normalized expression level of the at least second gene; comparing $\Delta_{expression}$ to a predetermined cutoff value; and administering to the subject at least one therapeutically effective amount of at least one first therapy when $\Delta_{expression}$ is greater than the predetermined cutoff value.

The present disclosure provides a method of treating bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the least one reference value to obtain a normalized expression level of the first gene; normalizing the expression level of the at least second gene to the at least one reference value to obtain a normalized expression level of the at least second gene; determining $\Delta_{expression}$, wherein $\Delta_{expression}$ is the difference between the normalized expression level of the first gene and the normalized expression level of the at least second gene; comparing $\Delta_{expression}$ to a predetermined cutoff value; and administering to the subject at least one therapeutically effective amount of at least one first therapy when $\Delta_{expression}$ is greater than the predetermined cutoff value.

The present disclosure provides a method of treating bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining $\Delta_{expression}$, wherein $\Delta_{expression}$ is the difference between the expression level of the first gene and the expression level of the at least second gene; comparing $\Delta_{expression}$ to a predetermined cutoff value; and administering to the subject at least one therapeutically effective amount of at least one first therapy when $\Delta_{expression}$ is greater than the predetermined cutoff value.

The present disclosure provides a method of identifying the presence or absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the at least second gene to the expression level of the at least one reference gene to obtain a normalized expression level of the at least second gene; determining $\Delta_{expression}$, wherein $\Delta_{expression}$ is the difference between the normalized expression level of the first gene and the normalized expression level of the at least second gene; comparing $\Delta_{expression}$ to a predetermined cutoff value; and identifying the presence of bladder cancer in the subject when $\Delta_{expression}$ is less than the predetermined cutoff value or identifying the absence of bladder cancer in the subject when $\Delta_{expression}$ is greater than or equal to the predetermined cutoff.

The present disclosure provides a method of identifying the presence or absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the at least second gene to the at least one reference value to obtain a normalized expression level of the at least second gene; determining $\Delta_{expression}$, wherein $\Delta_{expression}$ is the difference between the normalized expression level of the first gene and the normalized expression level of the at least second gene; comparing $\Delta_{expression}$ to a predetermined cutoff value; and identifying the presence of bladder cancer in the subject when $\Delta_{expression}$ is less than the predetermined cutoff value or identifying the absence of bladder cancer in the subject when $\Delta_{expression}$ is greater than or equal to the predetermined cutoff.

The present disclosure provides a method of identifying the presence or absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining $\Delta_{expression}$, wherein $\Delta_{expression}$ is the difference between the expression level of the first gene and the expression level of the at least second gene; comparing $\Delta_{expression}$ to a predetermined cutoff value; and identifying the presence of bladder cancer in the subject when $\Delta_{expression}$ is less than the predetermined cutoff value or identifying the absence of bladder cancer in the subject when $\Delta_{expression}$ is greater than or equal to the predetermined cutoff.

The present disclosure provides a method of treating bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the at least second gene to the expression level of the at least one reference gene to obtain a normalized expression level of the at least second gene; determining $\Delta_{expression}$, wherein $\Delta_{expression}$ is the difference between the normalized expression level of the first gene and the normalized expression level of the at least second gene; comparing $\Delta_{expression}$ to a predetermined cutoff value; and administering to the subject at least one therapeutically effective amount of at least one first therapy when $\Delta_{expression}$ is less than the predetermined cutoff value.

The present disclosure provides a method of treating bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the at least second gene to the at least one reference value to obtain a normalized expression level of the at least second gene; determining $\Delta_{expression}$, wherein $\Delta_{expression}$ is the difference between the normalized expression level of the first gene and the normalized expression level of the at least second gene; comparing $\Delta_{expression}$ to a predetermined cutoff value; and administering to the subject at least one therapeutically effective amount of at least one first therapy when $\Delta_{expression}$ is less than the predetermined cutoff value.

The present disclosure provides a method of treating bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining $\Delta_{expression}$, wherein $\Delta_{expression}$ is the difference between the expression level of the first gene and the expression level of the at least second gene; comparing $\Delta_{expression}$ to a predetermined cutoff value; and administering to the subject at least one therapeutically effective amount of at least one first therapy when $\Delta_{expression}$ is less than the predetermined cutoff value.

The present disclosure provides a method of determining the risk of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the at least second gene to the expression level of the at least one reference gene to obtain a normalized expression level of the at least second gene; determining $\Delta_{expression}$, wherein $\Delta_{expression}$ is the difference between the normalized expression level of the first gene and the normalized expression level of the at least second gene; and determining the risk of bladder cancer in the subject based on $\Delta_{expression}$.

The present disclosure provides a method of determining the risk of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the at least second gene to the at least one reference value to obtain a normalized expression level of the at least second gene; determining $\Delta_{expression}$, wherein $\Delta_{expression}$ is the difference between the normalized expression level of the first gene and the normalized expression level of the at least second gene; and determining the risk of bladder cancer in the subject based on $\Delta_{expression}$.

The present disclosure provides a method of determining the risk of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining $\Delta_{expression}$, wherein $\Delta_{expression}$ is the difference between the expression level of the first gene and the expression level of the at least second gene; and determining the risk of bladder cancer in the subject based on $\Delta_{expression}$.

The present disclosure provides a method of identifying the presence bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the at least second gene to the expression level of the at least one reference gene to obtain a normalized expression level of the at least second gene; determining $\Delta_{expression}$, wherein $\Delta_{expression}$ is the difference between the normalized expression level of the first gene and the normalized expression level of the at least second gene; and comparing $\Delta_{expression}$ to a predetermined cutoff value.

The present disclosure provides a method of identifying the presence bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the at least second gene to the at least one reference value to obtain a normalized expression level of the at least second gene; determining $\Delta_{expression}$, wherein $\Delta_{expression}$ is the difference between the normalized expression level of the first gene and the normalized expression level of the at least second gene; and comparing $\Delta_{expression}$ to a predetermined cutoff value.

In some aspects, the preceding methods can further comprise identifying the presence of bladder cancer in the subject when $\Delta_{expression}$ is greater than the predetermined cutoff value. In some aspects, the preceding methods can further comprise identifying the presence of bladder cancer in the subject when $\Delta_{expression}$ is greater than or equal to the predetermined cutoff value. In some aspects, the preceding methods can further comprise identifying the presence of bladder cancer in the subject when $\Delta_{expression}$ is less than the predetermined cutoff value. In some aspects, the preceding methods can further comprise identifying the presence of bladder cancer in the subject when $\Delta_{expression}$ is less than or equal to the predetermined cutoff value.

The present disclosure provides a method of identifying the presence bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining $\Delta_{expression}$, wherein $\Delta_{expression}$ is the difference between the expression level of the first gene and the expression level of the at least second gene; and comparing $\Delta_{expression}$ to a predetermined cutoff value.

In some aspects, the preceding method can further comprise identifying the presence of bladder cancer in the subject when $\Delta_{expression}$ is greater than the predetermined cutoff value. In some aspects, the preceding method can further comprise identifying the presence of bladder cancer in the subject when $\Delta_{expression}$ is greater than or equal to the predetermined cutoff value. In some aspects, the preceding method can further comprise identifying the presence of bladder cancer in the subject when $\Delta_{expression}$ is less than the predetermined cutoff value. In some aspects, the preceding method can further comprise identifying the presence of bladder cancer in the subject when $\Delta_{expression}$ is less than or equal to the predetermined cutoff value.

The present disclosure provides a method of treating bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the at least second gene to the expression level of the at least one reference gene to obtain a normalized expression level of the at least second gene; determining $\Delta_{expression}$, wherein $\Delta_{expression}$ is the difference between the normalized expression level of the first gene and the normalized expression level of the at least second gene; and comparing $\Delta_{expression}$ to a predetermined cutoff value.

The present disclosure provides a method of treating bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the at least second gene to the at least one reference value to obtain a normalized expression level of the at least second gene; determining $\Delta_{expression}$, wherein $\Delta_{expression}$ is the difference between the normalized expression level of the first gene and the normalized expression level of the at least second gene; and comparing expression to a predetermined cutoff value.

In some aspects, the preceding methods can further comprise administering to the subject at least one therapeutically effective amount of at least one first therapy when $\Delta_{expression}$ is greater than the predetermined cutoff value. In some aspects, the preceding methods can further comprise administering to the subject at least one therapeutically effective amount of at least one first therapy when $\Delta_{expression}$ is greater than or equal to the predetermined cutoff value. In some aspects, the preceding methods can further comprise administering to the subject at least one therapeutically effective amount of at least one first therapy when $\Delta_{expression}$ is less than the predetermined cutoff value. In some aspects, the preceding methods can further comprise administering to the subject at least one therapeutically effective amount of at least one first therapy when $\Delta_{expression}$ is less than or equal to the predetermined cutoff value.

The present disclosure provides a method of treating bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining Δexpression, wherein Δexpression is the difference between the expression level of the first gene and the expression level of the at least second gene; and comparing $\Delta_{expression}$ to a predetermined cutoff value.

In some aspects, the preceding method can further comprise administering to the subject at least one therapeutically effective amount of at least one first therapy when $\Delta_{expression}$ is greater than the predetermined cutoff value. In some aspects, the preceding method can further comprise administering to the subject at least one therapeutically effective amount of at least one first therapy when $\Delta_{expression}$ is greater than or equal to the predetermined cutoff value. In some aspects, the preceding method can further comprise administering to the subject at least one therapeutically effective amount of at least one first therapy when $\Delta_{expression}$ is less than the predetermined cutoff value. In some aspects, the preceding method can further comprise administering to the subject at least one therapeutically effective amount of at least one first therapy when $\Delta_{expression}$ is less than or equal to the predetermined cutoff value.

The present disclosure provides a method of identifying the absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the at least second gene to the expression level of the at least one reference gene to obtain a normalized expression level of the at least second gene; determining $\Delta_{expression}$, wherein expression is the difference between the normalized expression level of the first gene and the normalized expression level of the at least second gene; and comparing $\Delta_{expression}$ to a predetermined cutoff value.

The present disclosure provides a method of identifying the absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the at least second gene to the at least one reference value to obtain a normalized expression level of the at least second gene; determining $\Delta_{expression}$, wherein $\Delta_{expression}$ is the difference between the normalized expression level of the first gene and the normalized expression level of the at least second gene; and comparing $\Delta_{expression}$ to a predetermined cutoff value.

In some aspects, the preceding methods can further comprise identifying the absence of bladder cancer in the subject when $\Delta_{expression}$ is greater than the predetermined cutoff value. In some aspects, the preceding methods can further comprise identifying the absence of bladder cancer in the subject when $\Delta_{expression}$ is greater than or equal to the predetermined cutoff value. In some aspects, the preceding methods can further comprise identifying the absence of bladder cancer in the subject when $\Delta_{expression}$ is less than the predetermined cutoff value. In some aspects, the preceding methods can further comprise identifying the absence of bladder cancer in the subject when $\Delta_{expression}$ is less than or equal to the predetermined cutoff value.

The present disclosure provides a method of identifying the absence of bladder cancer in a subject comprising: determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining $\Delta_{expression}$, wherein $\Delta_{expression}$ is the difference between the expression level of the first gene and the expression level of the at least second gene; and comparing $\Delta_{expression}$ to a predetermined cutoff value.

In some aspects, the preceding method can further comprise identifying the absence of bladder cancer in the subject when $\Delta_{expression}$ is greater than the predetermined cutoff value. In some aspects, the preceding method can further comprise identifying the absence of bladder cancer in the subject when $\Delta_{expression}$ is greater than or equal to the predetermined cutoff value. In some aspects, the preceding method can further comprise identifying the absence of bladder cancer in the subject when $\Delta_{expression}$ is less than the predetermined cutoff value. In some aspects, the preceding method can further comprise identifying the absence of bladder cancer in the subject when $\Delta_{expression}$ is less than or equal to the predetermined cutoff value.

The present disclosure provides a method of determining the risk of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; and determining the risk of bladder cancer in the subject based on $\Delta_{expression}$ and the normalized expression level of the at least third gene.

The present disclosure provides a method of determining the risk of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; and determining the risk of bladder cancer in the subject based on $\Delta_{expression}$ and the normalized expression level of the at least third gene.

The present disclosure provides a method of determining the risk of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; determining the risk of bladder cancer in the subject based on $\Delta_{expression}$ and the normalized expression level of the at least third gene.

The present disclosure provides a method of determining the risk of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; and determining the risk of bladder cancer in the subject based on $\Delta_{expression}$ and the normalized expression level of the at least third gene.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is greater than the second predetermined cutoff value or identifying the absence of bladder cancer in the subject when $\Delta_{expression}$ is less than or equal to the first predetermined cutoff value and the normalized expression level of the at least third gene is less than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is greater than the second predetermined cutoff value or identifying the absence of bladder cancer in the subject when $\Delta_{expression}$ is less than or equal to the first predetermined cutoff value and the normalized expression level of the at least third gene is less than or equal to the second predetermined cutoff value.

The present disclosure provides a method of identifying the presence or absence of bladder cancer in a subject comprising: determining the expression level of a first, a second ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is greater than the second predetermined cutoff value or identifying the absence of bladder cancer in the subject when $\Delta_{expression}$ is less than or equal to the first predetermined cutoff value and the normalized expression level of the at least third gene is less than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is greater than the second predetermined cutoff value or identifying the absence of bladder cancer in the subject when $\Delta_{expression}$ is less than or equal to the first predetermined cutoff value and the normalized expression level of the at least third gene is less than or equal to the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is greater than the first predetermined cutoff value and the normalized expression level of the at least third gene is greater than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein expression is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is greater than the first predetermined cutoff value and the normalized expression level of the at least third gene is greater than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is greater than the first predetermined cutoff value and the normalized expression level of the at least third gene is greater than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is greater than the first predetermined cutoff value and the normalized expression level of the at least third gene is greater than the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is less than the second predetermined cutoff value or identifying the absence of bladder cancer in the subject when $\Delta_{expression}$ is less than or equal to the first predetermined cutoff value and the normalized expression level of the at least third gene is greater than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is less than the second predetermined cutoff value or identifying the absence of bladder cancer in the subject when $\Delta_{expression}$ is less than or equal to the first predetermined cutoff value and the normalized expression level of the at least third gene is greater than or equal to the second predetermined cutoff value.

The present disclosure provides a method of identifying the presence or absence of bladder cancer in a subject comprising: determining the expression level of a first, a second ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is less than the second predetermined cutoff value or identifying the absence of bladder cancer in the subject when $\Delta_{expression}$ is less than or equal to the first predetermined cutoff value and the normalized expression level of the at least third gene is greater than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is greater than the first predetermined cutoff value and the normalized expression level of the at least third gene is less than the second predetermined cutoff value or identifying the absence of bladder cancer in the subject when $\Delta_{expression}$ is less than or equal to the first predetermined cutoff value and the normalized expression level of the at least third gene is greater than or equal to the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is greater than the first predetermined cutoff value and the normalized expression level of the at least third gene is less than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is greater than the first predetermined cutoff value and the normalized expression level of the at least third gene is less than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is greater than the first predetermined cutoff value and the normalized expression level of the at least third gene is less than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is greater than the first predetermined cutoff value and the normalized expression level of the at least third gene is less than the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is less than the first predetermined cutoff value and the normalized expression level of the at least third gene is greater than the second predetermined cutoff value or identifying the absence of bladder cancer in the subject when $\Delta_{expression}$ is greater than or equal to the first predetermined cutoff value and the normalized expression level of the at least third gene is less than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is less than the first predetermined cutoff value and the normalized expression level of the at least third gene is greater than the second predetermined cutoff value or identifying the absence of bladder cancer in the subject when $\Delta_{expression}$ is greater than or equal to the first predetermined cutoff value and the normalized expression level of the at least third gene is less than or equal to the second predetermined cutoff value.

The present disclosure provides a method of identifying the presence or absence of bladder cancer in a subject comprising: determining the expression level of a first, a second or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is less than the first predetermined cutoff value and the normalized expression level of the at least third gene is greater than the second predetermined cutoff value or identifying the absence of bladder cancer in the subject when $\Delta_{expression}$ is greater than or equal to the first predetermined cutoff value and the normalized expression level of the at least third gene is less than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is less than the first predetermined cutoff value and the normalized expression level of the at least third gene is greater than the second predetermined cutoff value or identifying the absence of bladder cancer in the subject when $\Delta_{expression}$ is greater than or equal to the first predetermined cutoff value and the normalized expression level of the at least third gene is less than or equal to the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing expression to a first predetermined cutoff value; comparing the normalized expression level of the at least third gene to a second predetermined cutoff value; and administering to the subject at least one therapeutically effective amount of at least one first therapy when $\Delta_{expression}$ is less than the first predetermined cutoff value and the normalized expression level of the at least third gene is greater than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; comparing expression to a first predetermined cutoff value; comparing the normalized expression level of the at least third gene to a second predetermined cutoff value; and administering to the subject at least one therapeutically effective amount of at least one first therapy when $\Delta_{expression}$ is less than the first predetermined cutoff value and the normalized expression level of the at least third gene is greater than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is less than the first predetermined cutoff value and the normalized expression level of the at least third gene is greater than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is less than the first predetermined cutoff value and the normalized expression level of the at least third gene is greater than the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing expression to a first predetermined cutoff value; comparing the normalized expression level of the at least third gene to a second predetermined cutoff value; and identifying the presence of bladder cancer in the subject when $\Delta_{expression}$ is less than the first predetermined cutoff value and the normalized expression level of the at least third gene is less than the second predetermined cutoff value or identifying the absence of bladder cancer in the subject when $\Delta_{expression}$ is greater than or equal to the first predetermined cutoff value and the normalized expression level of the at least third gene is greater than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is less than the first predetermined cutoff value and the normalized expression level of the at least third gene is less than the second predetermined cutoff value or identifying the absence of bladder cancer in the subject when $\Delta_{expression}$ is greater than or equal to the first predetermined cutoff value and the normalized expression level of the at least third gene is greater than or equal to the second predetermined cutoff value.

The present disclosure provides a method of identifying the presence or absence of bladder cancer in a subject comprising: determining the expression level of a first, a second or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is less than the first predetermined cutoff value and the normalized expression level of the at least third gene is less than the second predetermined cutoff value or identifying the absence of bladder cancer in the subject when $\Delta_{expression}$ is greater than or equal to the first predetermined cutoff value and the normalized expression level of the at least third gene is greater than or equal to the second predetermined cutoff value.

The present disclosure provides a method of identifying the presence or absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and identifying the presence of bladder cancer in the subject when $\Delta_{expression}$ is less than the first predetermined cutoff value and the normalized expression level of the at least third gene is less than the second predetermined cutoff value or identifying the absence of bladder cancer in the subject when $\Delta_{expression}$ is greater than or equal to the first predetermined cutoff value and the normalized expression level of the at least third gene is greater than or equal to the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is less than the first predetermined cutoff value and the normalized expression level of the at least third gene is less than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is less than the first predetermined cutoff value and the normalized expression level of the at least third gene is less than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is less than the first predetermined cutoff value and the normalized expression level of the at least third gene is less than the second predetermined cutoff value.

The present disclosure provides a method of treating bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; comparing the normalized expression level of the at least third gene to a second predetermined cutoff value; and administering to the subject at least one therapeutically effective amount of at least one first therapy when $\Delta_{expression}$ is less than the first predetermined cutoff value and the normalized expression level of the at least third gene is less than the second predetermined cutoff value.

The present disclosure provides a method of identifying the presence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; and comparing the normalized expression level of the at least third gene to a second predetermined cutoff value.

The present disclosure provides a method of identifying the presence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; and comparing the normalized expression level of the at least third gene to a second predetermined cutoff value.

In some aspects, the preceding methods can further comprise identifying the presence of bladder cancer in the subject when $\Delta_{expression}$ is greater than the first predetermined cutoff value and the normalized expression level of the at least third gene is greater than the second predetermined cutoff value. In some aspects, the preceding methods can further comprise identifying the presence of bladder cancer in the subject when $\Delta_{expression}$ is greater than the first predetermined cutoff value and the normalized expression level of the at least third gene is less than the second predetermined cutoff value. In some aspects, the preceding methods can further comprise identifying the presence of bladder cancer in the subject when $\Delta_{expression}$ is less than the first predetermined cutoff value and the normalized expression level of the at least third gene is greater than the second predetermined cutoff value. In some aspects, the preceding methods can further comprise identifying the presence of bladder cancer in the subject when $\Delta_{expression}$ is less than the first predetermined cutoff value and the normalized expression level of the at least third gene is less than the second predetermined cutoff value.

In some aspects, the preceding methods can further comprise administering to the subject at least one therapeutically effective amount of at least one first therapy when $\Delta_{expression}$ is greater than the first predetermined cutoff value and the normalized expression level of the at least third gene is greater than the second predetermined cutoff value. In some aspects, the preceding methods can further comprise administering to the subject at least one therapeutically effective amount of at least one first therapy when $\Delta_{expression}$ is greater than the first predetermined cutoff value and the normalized expression level of the at least third gene is less than the second predetermined cutoff value. In some aspects, the preceding methods can further comprise administering to the subject at least one therapeutically effective amount of at least one first therapy when $\Delta_{expression}$ is less than the first predetermined cutoff value and the normalized expression level of the at least third gene is greater than the second predetermined cutoff value. In some aspects, the preceding methods can further comprise administering to the subject at least one therapeutically effective amount of at least one first therapy when $\Delta_{expression}$ is less than the first predetermined cutoff value and the normalized expression level of the at least third gene is less than the second predetermined cutoff value.

The present disclosure provides a method of identifying the presence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; and comparing the normalized expression level of the at least third gene to a second predetermined cutoff value.

The present disclosure provides a method of identifying the presence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; and comparing the normalized expression level of the at least third gene to a second predetermined cutoff value.

In some aspects, the preceding methods can further comprise identifying the presence of bladder cancer in the subject when $\Delta_{expression}$ is greater than the first predetermined cutoff value and the normalized expression level of the at least third gene is greater than the second predetermined cutoff value. In some aspects, the preceding methods can further comprise identifying the presence of bladder cancer in the subject when $\Delta_{expression}$ is greater than the first predetermined cutoff value and the normalized expression level of the at least third gene is less than the second predetermined cutoff value. In some aspects, the preceding methods can further comprise identifying the presence of bladder cancer in the subject when $\Delta_{expression}$ is less than the first predetermined cutoff value and the normalized expression level of the at least third gene is greater than the second predetermined cutoff value. In some aspects, the preceding methods can further comprise identifying the presence of bladder cancer in the subject when $\Delta_{expression}$ is less than the first predetermined cutoff value and the normalized expression level of the at least third gene is less than the second predetermined cutoff value.

In some aspects, the preceding methods can further comprise administering to the subject at least one therapeutically effective amount of at least one first therapy when $\Delta_{expression}$ is greater than the first predetermined cutoff value and the normalized expression level of the at least third gene is greater than the second predetermined cutoff value. In some aspects, the preceding methods can further comprise administering to the subject at least one therapeutically effective amount of at least one first therapy when $\Delta_{expression}$ is greater than the first predetermined cutoff value and the normalized expression level of the at least third gene is less than the second predetermined cutoff value. In some aspects, the preceding methods can further comprise administering to the subject at least one therapeutically effective amount of at least one first therapy when $\Delta_{expression}$ is less than the first predetermined cutoff value and the normalized expression level of the at least third gene is greater than the second predetermined cutoff value. In some aspects, the preceding methods can further comprise administering to the subject at least one therapeutically effective amount of at least one first therapy when $\Delta_{expression}$ is less than the first predetermined cutoff value and the normalized expression level of the at least third gene is less than the second predetermined cutoff value.

The present disclosure provides a method of identifying the absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the first gene to the expression level of the at least one reference gene to obtain a normalized expression level of the first gene; normalizing the expression level of the second gene to the expression level of the at least one reference gene to obtain a normalized expression level of the second gene; normalizing the expression level of the at least third gene to the expression level of the at least one reference gene to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; and comparing the normalized expression level of the at least third gene to a second predetermined cutoff value.

The present disclosure provides a method of identifying the absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the first gene to the at least one reference value to obtain a normalized expression level of the first gene; normalizing the expression level of the second gene to the at least one reference value to obtain a normalized expression level of the second gene; normalizing the expression level of the at least third gene to the at least one reference value to obtain a normalized expression level of the at least third gene; determining $\Delta_{expression}$, wherein $\Delta_{expression}$ is the difference between the normalized expression level of the first gene and the normalized expression level of the at least second gene; comparing $\Delta_{expression}$ to a first predetermined cutoff value; and comparing the normalized expression level of the at least third gene to a second predetermined cutoff value.

In some aspects, the preceding methods can further comprise identifying the absence of bladder cancer in the subject when $\Delta_{expression}$ is greater than the first predetermined cutoff value and the normalized expression level of the at least third gene is greater than the second predetermined cutoff value. In some aspects, the preceding methods can further comprise identifying the absence of bladder cancer in the subject when $\Delta_{expression}$ is greater than the first predetermined cutoff value and the normalized expression level of the at least third gene is less than the second predetermined cutoff value. In some aspects, the preceding methods can further comprise identifying the absence of bladder cancer in the subject when $\Delta_{expression}$ is less than the first predetermined cutoff value and the normalized expression level of the at least third gene is greater than the second predetermined cutoff value. In some aspects, the preceding methods can further comprise identifying the absence of bladder cancer in the subject when $\Delta_{expression}$ is less than the first predetermined cutoff value and the normalized expression level of the at least third gene is less than the second predetermined cutoff value.

In some aspects of the preceding method, the first gene can be UPK2, the second gene can be OSR1, the at least third gene can be KRT20 and the at least one reference gene can be DHRS2. Thus, the present disclosure provides a method of identifying the absence of bladder cancer in a subject comprising: determining the expression level of UPK2, OSR1 and KRT20 and the expression level of the least one reference gene DHRS2 in a biological sample from the subject; normalizing the expression level of UPK2 to the expression level of DHRS2 to obtain a normalized expression level UPK2; normalizing the expression level of OSR1 to the expression level of DHRS2 to obtain a normalized expression level of OSR1; normalizing the expression level of KRT20 to the expression level of DHRS2 to obtain a normalized expression level of KRT20; determining $\Delta_{expression}$, wherein $\Delta_{expression}$ is the difference between the normalized expression level of UPK2 and the normalized expression level of OSR1; comparing $\Delta_{expression}$ to a first predetermined cutoff value; and comparing the normalized expression level of KRT20 to a second predetermined cutoff value; and identifying the absence of bladder cancer in the subject when $\Delta_{expression}$ is less than the first predetermined cutoff value and the normalized expression level of KRT20 is greater than the second predetermined cutoff value.

The present disclosure provides a method of identifying the absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject; normalizing the expression level of the at least third gene to the expression level of the at least one reference gene to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; and comparing the normalized expression level of the at least third gene to a second predetermined cutoff value.

The present disclosure provides a method of identifying the absence of bladder cancer in a subject comprising: determining the expression level of a first, a second gene and at least a third gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject; determining at least one reference value in the biological sample; normalizing the expression level of the at least third gene to the at least one reference value to obtain a normalized expression level of the at least third gene; determining $\Delta_{expression}$, wherein $\Delta_{expression}$ is the difference between the expression level of the first gene and the expression level of the at least second gene; comparing $\Delta_{expression}$ to a first predetermined cutoff value; and comparing the normalized expression level of the at least third gene to a second predetermined cutoff value.

In some aspects, the preceding methods can further comprise identifying the absence of bladder cancer in the subject when $\Delta_{expression}$ is greater than the first predetermined cutoff value and the normalized expression level of the at least third gene is greater than the second predetermined cutoff value. In some aspects, the preceding methods can further comprise identifying the absence of bladder cancer in the subject when $\Delta_{expression}$ is greater than the first predetermined cutoff value and the normalized expression level of the at least third gene is less than the second predetermined cutoff value. In some aspects, the preceding methods can further comprise identifying the absence of bladder cancer in the subject when $\Delta_{expression}$ is less than the first predetermined cutoff value and the normalized expression level of the at least third gene is greater than the second predetermined cutoff value. In some aspects, the preceding methods can further comprise identifying the absence of bladder cancer in the subject when $\Delta_{expression}$ is less than the first predetermined cutoff value and the normalized expression level of the at least third gene is less than the second predetermined cutoff value.

In some aspects of the preceding method, the first gene can be UPK2, the second gene can be OSR1, the at least third gene can be KRT20 and the at least one reference gene can be DHRS2. Thus, the present disclosure provides a method of identifying the absence of bladder cancer in a subject comprising: determining the expression level of UPK2, OSR1 and KRT20 and the expression level of the least one reference gene DHRS2 in a biological sample from the subject; normalizing the expression level of KRT20 to the expression level of DHRS2 to obtain a normalized expression level of KRT20; determining $\Delta_{expression}$, wherein $\Delta_{expression}$ is the difference between the expression level of UPK2 and the expression level of OSR1; comparing $\Delta_{expression}$ to a first predetermined cutoff value; and comparing the normalized expression level of KRT20 to a second predetermined cutoff value; and identifying the absence of bladder cancer in the subject when $\Delta_{expression}$ is less than the first predetermined cutoff value and the normalized expression level of KRT20 is greater than the second predetermined cutoff value.

The present disclosure provides a method comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject at a first time point; determining the expression level of the at least one gene and the expression level of the at least one reference gene in a biological sample from the subject at a second time point; normalizing the expression level of the at least one gene at the first time point to the expression level of the at least one reference gene at the first time point to obtain a normalized expression level of the at least one gene at the first time point; normalizing the expression level of the at least one gene at the second time point to the expression level of the at least one reference gene at the second time point to obtain a normalized expression level of the at least one gene at the second time point; and comparing the normalized expression level of the at least one gene at the first time point to the normalized expression level of the at least one gene at the second time point.

The present disclosure provides a method comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and determining at least one reference value in a biological sample from the subject at a first time point; determining the expression level of the at least one gene and the at least one reference value in a biological sample from the subject at a second time point; normalizing the expression level of the at least one gene at the first time point to the at least one reference value at the first time point to obtain a normalized expression level of the at least one gene at the first time point; normalizing the expression level of the at least one gene at the second time point to the at least one reference value at the second time point to obtain a normalized expression level of the at least one gene at the second time point; and comparing the normalized expression level of the at least one gene at the first time point to the normalized expression level of the at least one gene at the second time point.

In some aspects of the preceding methods, the first time point can be before administration of at least one first therapy to the subject and the second time point can be after the administration of at least one first therapy to the subject. By comparing the normalized expression level of the at least one gene at the first time point to the normalized expression level of the at least one gene at the second time point, the efficacy of the at least one first therapy can be evaluated to determine whether the subject should continue to receive the at least one first therapy.

In a non-limiting example, the at least one first therapy can be continued to be administered to the subject when the normalized expression level of the at least one gene at the first time point is greater than the normalized expression level of the at least one gene at the second time point. In another non-limiting example, the at least one first therapy can be continued to be administered to the subject when the normalized expression level of the at least one gene at the first time point is less than the normalized expression level of the at least one gene at the second time point.

In a non-limiting example, the at least one first therapy can be discontinued and an at least one second therapy can be administered to the subject when the normalized expression level of the at least one gene at the first time point is greater than the normalized expression level of the at least one gene at the second time point. In another non-limiting example, the at least one first therapy can be discontinued and an at least one second therapy can be administered to the subject when the normalized expression level of the at least one gene at the first time point is less than the normalized expression level of the at least one gene at the second time point.

In some aspects, the preceding methods can comprise determining the expression of at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB.

The present disclosure provides a method comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject at a first time point; determining the expression level of the at least one gene and the expression level of the at least one reference gene in a biological sample from the subject at a second time point; normalizing the expression level of the at least one gene at the first time point to the expression level of the at least one reference gene at the first time point to obtain a normalized expression level of the at least one gene at the first time point; normalizing the expression level of the at least one gene at the second time point to the expression level of the at least one reference gene at the second time point to obtain a normalized expression level of the at least one gene at the second time point; determining $\Delta_{expression}$, wherein $\Delta_{expression}$ is the difference between the normalized expression level of the at least one gene at the first time point and the normalized expression level of the at least one gene at the second time point; and comparing $\Delta_{expression}$ to a predetermined cutoff value.

The present disclosure provides a method comprising: determining the expression level of at least one gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and determining at least one reference value in a biological sample from the subject at a first time point; determining the expression level of the at least one gene and the at least one reference value in a biological sample from the subject at a second time point; normalizing the expression level of the at least one gene at the first time point to the at least one reference value at the first time point to obtain a normalized expression level of the at least one gene at the first time point; normalizing the expression level of the at least one gene at the second time point to the at least one reference value at the second time point to obtain a normalized expression level of the at least one gene at the second time point; determining $\Delta_{expression}$, wherein $\Delta_{expression}$ is the difference between the normalized expression level of the at least one gene at the first time point and the normalized expression level of the at least one gene at the second time point; and comparing $\Delta_{expression}$ to a predetermined cutoff value.

In some aspects of the preceding methods, the first time point can be before administration of at least one first therapy to the subject and the second time point can be after the administration of at least one first therapy to the subject. By comparing $\Delta_{expression}$ to a predetermined cutoff value, the efficacy of the at least one first therapy can be evaluated to determine whether the subject should continue to receive the at least one first therapy.

In a non-limiting example, the at least one first therapy can be continued to be administered to the subject when $\Delta_{expression}$ is greater than the predetermined cutoff value. In another non-limiting example, the at least one first therapy can be continued to be administered to the subject when $\Delta_{expression}$ is less than the predetermined cutoff value.

In a non-limiting example, the at least one first therapy can be discontinued and an at least one second therapy can be administered to the subject when $\Delta_{expression}$ is greater than the predetermined cutoff value. In another non-limiting example, the at least one first therapy can be discontinued and an at least one second therapy can be administered to the subject when $\Delta_{expression}$ is greater than the predetermined cutoff value.

In some aspects, the preceding methods can comprise determining the expression of at least two genes, or at least three genes, or at least four genes or at least five genes, or at least six genes, or at least seven genes, or at least eight genes, or at least nine genes, or at least ten genes, or at least 11 genes, or at least 12 genes, or at least 13 genes, or at least 14 genes, or at least 15 genes, or at least 16 genes selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB.

The present disclosure provides a method comprising determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject at a first time point; determining the expression level of the first, the at least second gene and the at least one reference gene in a biological sample from the subject at a second time point; normalizing the expression level of the first gene at the first time point to the expression level of the at least one reference gene at the first time point to obtain a normalized expression level of the first gene at the first time point and normalizing the expression level of the at least second gene at the first time point to the expression level of the at least one reference gene at the first time point to obtain a normalized expression level of the at least second gene at the first time point; determining $\Delta_{expression\_1}$, wherein $\Delta_{expression\_1}$ is the difference between the normalized expression level of the first gene at the first time point and the normalized expression level of the at least second gene at the first time point; normalizing the expression level of the first gene at the second time point to the expression level of the at least one reference gene at the second time point to obtain a normalized expression level of the first gene at the second time point and normalizing the expression level of the at least second gene at the second time point to the expression level of the at least one reference gene at the second time point to obtain a normalized expression level of the at least second gene at the second time point; determining $\Delta_{expression\_2}$, wherein $\Delta_{expression\_2}$ is the difference between the normalized expression level of the first gene at the second time point and the normalized expression level of the at least second gene at the second time point; and comparing $\Delta_{expression\_1}$ to $\Delta_{expression\_2}$.

The present disclosure provides a method comprising determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and determining at least one reference value in a biological sample from the subject at a first time point; determining the expression level of the first, the expression level of the at least second gene and the at least one reference value in a biological sample from the subject at a second time point; normalizing the expression level of the first gene at the first time point to the at least one reference value at the first time point to obtain a normalized expression level of the first gene at the first time point and normalizing the expression level of the at least second gene at the first time point to the at least one reference value at the first time point to obtain a normalized expression level of the at least second gene at the first time point; determining $\Delta_{expression\_1}$, wherein $\Delta_{expression\_1}$ is the difference between the normalized expression level of the first gene at the first time point and the normalized expression level of the at least second gene at the first time point; normalizing the expression level of the first gene at the second time point to the at least one reference value at the second time point to obtain a normalized expression level of the first gene at the second time point and normalizing the expression level of the at least second gene at the second time point to the at least one reference value at the second time point to obtain a normalized expression level of the at least second gene at the second time point; determining $\Delta_{expression\_2}$, wherein $\Delta_{expression\_2}$ is the difference between the normalized expression level of the first gene at the second time point and the normalized expression level of the at least second gene at the second time point; and comparing $\Delta_{expression\_1}$ to $\Delta_{expression\_2}$.

In some aspects of the preceding methods, the first time point can be before administration of at least one first therapy to the subject and the second time point can be after the administration of at least one first therapy to the subject. By comparing $\Delta_{expression\_1}$ to $\Delta_{expression\_2}$, the efficacy of the at least one first therapy can be evaluated to determine whether the subject should continue to receive the at least one first therapy.

In a non-limiting example, the at least one first therapy can be continued to be administered to the subject when $\Delta_{expression\_1}$ is greater than $\Delta_{expression\_2}$. In another non-limiting example, the at least one first therapy can be continued to be administered to the subject when $\Delta_{expression\_1}$ is less than $\Delta_{expression\_2}$.

In a non-limiting example, the at least one first therapy can be discontinued and an at least one second therapy can be administered to the subject when $\Delta_{expression\_1}$ is greater than $\Delta_{expression\_2}$. In another non-limiting example, the at least one first therapy can be discontinued and an at least one second therapy can be administered to the subject when $\Delta_{expression\_1}$ is greater than $\Delta_{expression\_2}$.

The present disclosure provides a method comprising determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject at a first time point; determining the expression level of the first and the at least second gene in a biological sample from the subject at a second time point; determining $\Delta_{expression\_1}$, wherein $\Delta_{expression\_1}$ is the difference between the expression level of the first gene at the first time point and the expression level of the at least second gene at the first time point; determining $\Delta_{expression\_2}$, wherein $\Delta_{expression\_2}$ is the difference between the expression level of the first gene at the second time point and the expression level of the at least second gene at the second time point; and comparing $\Delta_{expression\_1}$ to $\Delta_{expression\_2}$.

In some aspects of the preceding method, the first time point can be before administration of at least one first therapy to the subject and the second time point can be after the administration of at least one first therapy to the subject. By comparing $\Delta_{expression\_1}$ to $\Delta_{expression\_2}$, the efficacy of the at least one first therapy can be evaluated to determine whether the subject should continue to receive the at least one first therapy.

In a non-limiting example, the at least one first therapy can be continued to be administered to the subject when $\Delta_{expression\_1}$ is greater than $\Delta_{expression\_2}$. In another non-limiting example, the at least one first therapy can be continued to be administered to the subject when $\Delta_{expression\_1}$ is less than $\Delta_{expression}2$.

In a non-limiting example, the at least one first therapy can be discontinued and an at least one second therapy can be administered to the subject when $\Delta_{expression\_1}$ is greater than $\Delta_{expression\_2}$. In another non-limiting example, the at least one first therapy can be discontinued and an at least one second therapy can be administered to the subject when $\Delta_{expression\_1}$ is greater than $\Delta_{expression\_2}$.

The present disclosure provides a method comprising determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and the expression level of at least one reference gene in a biological sample from the subject at a first time point; determining the expression level of the first, the at least second gene and the at least one reference gene in a biological sample from the subject at a second time point; normalizing the expression level of the first gene at the first time point to the expression level of the at least one reference gene at the first time point to obtain a normalized expression level of the first gene at the first time point and normalizing the expression level of the at least second gene at the first time point to the expression level of the at least one reference gene at the first time point to obtain a normalized expression level of the at least second gene at the first time point; determining $\Delta_{expression\_1}$, wherein $\Delta_{expression\_1}$ is the difference between the normalized expression level of the first gene at the first time point and the normalized expression level of the at least second gene at the first time point; normalizing the expression level of the first gene at the second time point to the expression level of the at least one reference gene at the second time point to obtain a normalized expression level of the first gene at the second time point and normalizing the expression level of the at least second gene at the second time point to the expression level of the at least one reference gene at the second time point to obtain a normalized expression level of the at least second gene at the second time point; determining $\Delta_{expression\_2}$, wherein $\Delta_{expression\_2}$ is the difference between the normalized expression level of the first gene at the second time point and the normalized expression level of the at least second gene at the second time point; determining $\Delta\Delta_{expression}$, wherein $\Delta\Delta_{expression}$ is the difference between $\Delta_{expression\_1}$ to $\Delta_{expression\_2}$; and comparing $\Delta\Delta_{expression}$ to a predetermined cutoff value.

The present disclosure provides a method comprising determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB and determining at least one reference value in a biological sample from the subject at a first time point; determining the expression level of the first, the expression level of the at least second gene and the at least one reference value in a biological sample from the subject at a second time point; normalizing the expression level of the first gene at the first time point to the at least one reference value at the first time point to obtain a normalized expression level of the first gene at the first time point and normalizing the expression level of the at least second gene at the first time point to the at least one reference value at the first time point to obtain a normalized expression level of the at least second gene at the first time point; determining $\Delta_{expression}1$, wherein $\Delta_{expression}1$ is the difference between the normalized expression level of the first gene at the first time point and the normalized expression level of the at least second gene at the first time point; normalizing the expression level of the first gene at the second time point to the at least one reference value at the second time point to obtain a normalized expression level of the first gene at the second time point and normalizing the expression level of the at least second gene at the second time point to the at least one reference value at the second time point to obtain a normalized expression level of the at least second gene at the second time point; determining $\Delta_{expression\_2}$, wherein $\Delta_{expression\_2}$ is the difference between the normalized expression level of the first gene at the second time point and the normalized expression level of the at least second gene at the second time point; determining $\Delta\Delta_{expression}$, wherein $\Delta\Delta_{expression}$ is the difference between $\Delta_{expression\_1}$ to $\Delta_{expression\_2}$; and comparing $\Delta\Delta_{expression}$ to a predetermined cutoff value.

In some aspects of the preceding methods, the first time point can be before administration of at least one first therapy to the subject and the second time point can be after the administration of at least one first therapy to the subject. By comparing $\Delta\Delta_{expression}$ to a predetermined cutoff value, the efficacy of the at least one first therapy can be evaluated to determine whether the subject should continue to receive the at least one first therapy.

In a non-limiting example, the at least one first therapy can be continued to be administered to the subject when $\Delta\Delta_{expression}$ is greater than the predetermined cutoff value. In another non-limiting example, the at least one first therapy can be continued to be administered to the subject when $\Delta\Delta_{expression}$ is less than the predetermined cutoff value.

In a non-limiting example, the at least one first therapy can be discontinued and an at least one second therapy can be administered to the subject when $\Delta\Delta_{expression}$ is greater than the predetermined cutoff value. In another non-limiting example, the at least one first therapy can be discontinued and an at least one second therapy can be administered to the subject when $\Delta\Delta_{expression}$ is greater than the predetermined cutoff value.

The present disclosure provides a method comprising determining the expression level of a first and at least a second gene selected from DHRS2, UPK2, UPK1A, KRT20, UPK1B, ACER2, SNX31, VGLL1, FER1L4, UPK3A, OSR1, GATA3, SCUBE2, GAPDH, ADAM15 or HBB in a biological sample from the subject at a first time point; determining the expression level of the first and the at least second gene in a biological sample from the subject at a second time point; determining $\Delta_{expression\_1}$, wherein $\Delta_{expression}1$ is the difference between the expression level of the first gene at the first time point and the expression level of the at least second gene at the first time point; determining $\Delta_{expression\_2}$, wherein $\Delta_{expression\_2}$ is the difference between the expression level of the first gene at the second time point and the expression level of the at least second gene at the second time point; determining $\Delta\Delta_{expression}$, wherein $\Delta\Delta_{expression}$ is the difference between $\Delta_{expression}1$ to $\Delta_{expression\_2}$; and comparing $\Delta\Delta_{expression}$ to a predetermined cutoff value.

In some aspects of the preceding method, the first time point can be before administration of at least one first therapy to the subject and the second time point can be after the administration of at least one first therapy to the subject. By comparing $\Delta\Delta_{expression}$ to a predetermined cutoff value, the efficacy of the at least one first therapy can be evaluated to determine whether the subject should continue to receive the at least one first therapy.

In a non-limiting example, the at least one first therapy can be continued to be administered to the subject when $\Delta\Delta_{expression}$ is greater than the predetermined cutoff value. In another non-limiting example, the at least one first therapy can be continued to be administered to the subject when $\Delta\Delta_{expression}$ is less than the predetermined cutoff value.

In a non-limiting example, the at least one first therapy can be discontinued and an at least one second therapy can be administered to the subject when $\Delta\Delta_{expression}$ is greater than the predetermined cutoff value. In another non-limiting example, the at least one first therapy can be discontinued and an at least one second therapy can be administered to the subject when $\Delta\Delta_{expression}$ is greater than the predetermined cutoff value.

In some aspects of any method of the present disclosure, an at least one reference gene can be DHRS2. In some aspects of any method of the present disclosure, an at least one reference can be selected from the group consisting of DHRS2, UPK2, UPK1A, KRT20, UPK1B, ACER2, SNX31, VGLL1, FER1L4, UPK3A, OSR1, GATA3, SCUBE2, GAPDH, ADAM15 and HBB.

In some aspects of any method of the present disclosure, an at least one reference value can be the total concentration of cfDNA in a biological sample. Thus, in some aspects of any method of the present disclosure, determining an at least one reference value can comprise determining the concentration of cfDNA in a biological sample.

In some aspects of any method of the present disclosure, an at least one reference value can be the abundance of at least one DNA molecule in a biological sample. The at least one DNA molecule can comprise a specific sequence, including, but not limited to, a defined region of the ribosomal DNA or other genomic or mitochondrial DNA. Thus, in some aspects of any method of the present disclosure, determining an at least one reference value can comprise determining the abundance of at least one DNA molecule in a biological sample. In some aspects of any method of the present disclosure, an at least one reference value can be the abundance of at least one RNA molecule in a biological sample. In some aspects of any method of the present disclosure, an at least one reference value can be the expression level of at least one reference gene in the biological sample.

In some aspects of any method of the present disclosure, an at least one reference value can be the total microvesicular RNA concentration in a biological sample. Thus, in some aspects of any method of the present disclosure, determining an at least one reference value can comprise determining the total microvesicular RNA concentration in a biological sample.

In some aspects of any method of the present disclosure, an at least one reference value can be the number of microvesicles in a biological sample. Thus, in some aspects of any method of the present disclosure, determining an at least one reference value can comprise determining the number of microvesicles in a biological sample. In some aspects, determining the number of microvesicles in a biological sample can comprise nanoparticle tracking analysis.

In some aspects of any method of the present disclosure, an at least one reference value can be the abundance of at least one protein in the biological sample. The at least one protein can be microvesicle-associated or free of association with microvesicles. Thus, in some aspects of any method of the present disclosure, determining an at least one reference value can comprise determining the abundance of at least one protein in the biological sample.

In some aspects of any method of the present disclosure, an at least one reference value can be the abundance of at least one metabolite in the biological sample. The at least one metabolite can be microvesicle-associated or free of association with microvesicles. Thus, in some aspects of any method of the present disclosure, determining an at least one reference value can comprise determining the abundance of at least one metabolite in the biological sample.

In some aspects of any method of the present disclosure, a reference value can be any type of biological measurement made in the biological sample that accounts for variability between subjects, variability between different samples from the same subject, or any combination therefore. In some aspects of any method of the present disclosure, a reference value is any type of biological measurement that is uncorrelated with a disease state of a subject. For example, a reference value is uncorrelated with either the presence or absence of a bladder cancer. In some aspects of any method of the present disclosure, a reference value is any type of biological measurement that is a confounder to the disease process itself.

In some aspects of any method of the present disclosure, a predetermined cutoff value can be, at least in part, selected based on the sex of the subject. For example, a predetermined cutoff value used for a male subject may be different than a predetermined cutoff value used for a female subject. In some aspects of any method of the present disclosure, a predetermined cutoff value can be, at least in part, selected based on the ethnicity of the subject. In some aspects, a predetermined cutoff value can be, at least in part, selected based on other disease risk factors exhibited by the subject. These disease risk factors can include, but are not limited to, family history of disease, weight, pre-existing conditions, ethnicity, sex, drug use, smoking, fluid intake, chronic bladder irritations, chronic bladder infections, bladder birth defects, genetic-predisposition, previous chemotherapy treatment, diet or any other disease risk factor known in the art.

In some aspects of any method of the present disclosure, bladder cancer can be recurrent bladder cancer. In some aspects of any method of the present disclosure, bladder cancer can be relapsed bladder cancer.

In some aspects of any method of the present disclosure, bladder cancer can be urothelial carcinoma, transitional cell carcinoma, papillary carcinoma, flat carcinoma, squamous cell carcinoma, adenocarcinoma, sarcoma, small cell carcinoma or any combination thereof.

In some aspects of any method of the present disclosure, bladder cancer can comprise tumors of the urinary tract, tumors of the portions of the kidney that connect the ureter, the ureters and the urethra or any combination thereof.

In some aspects of any method of the present disclosure, bladder cancer can be non-invasive bladder cancer, invasive bladder cancer, superficial bladder cancer, non-muscle invasive bladder cancer.

In some aspects of any method of the present disclosure, the bladder cancer can be stage 0a bladder cancer, stage I bladder cancer, stage II bladder cancer, stage III bladder cancer or stage IV bladder cancer.

In some aspects of any method of the present disclosure, a biological sample can comprise at least one nucleic acid. The at least one nucleic acid can comprise at least one cell-free nucleic acid. Cell-free nucleic acid can comprise cell-free DNA (cfDNA), cell-free RNA (cfRNA) or a combination of cfDNA and cfRNA. The at least one nucleic acid can comprise at least one microvesicular nucleic acid. A microvesicular nucleic acid is a nucleic acid molecule that has been extracted from the interior of a microvesicle that has been shed or has budded of from the plasma membrane of a eukaryotic or prokaryotic cell. A microvesicular nucleic acid molecule can be extracted from the interior of an exosome, an extracellular vesicle, a prostasome, a dexosome, a texosome, an ectosome, an oncosome, an apoptotic body, a retrovirus-like particle, or a human endogenous retrovirus (HERV) particle. A microvesicular nucleic acid can comprise microvesicular DNA, microvesicular RNA or a combination of microvesicular DNA and microvesicular RNA. In some aspects of any method of the present disclosure, a biological sample can comprise cell-free DNA and microvesicular RNA.

In some aspects of any method of the present disclosure, a microvesicular nucleic acid can be extracted from at least one microvesicle. In some aspects of any method of the present disclosure, a microvesicular nucleic acid can be extracted from a microvesicle fraction. A microvesicle or a microvesicle fraction can be isolated from a bodily fluid sample from a subject. A bodily fluid can be a fluid isolated from anywhere in the body of ta subject, such as, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. Biological samples can also include fecal or cecal samples, or supernatants isolated therefrom.

In some aspects of any method of the present disclosure, a biological sample can be a bodily fluid that has been filtered to remove cells and/or cellular debris. In a non-limiting example, a biological sample can be urine that has been filtered to remove cells and/or cellular debris.

In some aspects of any method of the present disclosure, a biological sample can comprise at least one microvesicular nucleic acid extracted from at least one microvesicle.

In some aspects, a bodily fluid sample comprises urine. In aspects wherein the bodily fluid sample comprises urine, the urine can comprise at least 0.05% blood, at least 0.5% blood, at least 1% blood, at least 1.5% blood, at least 2.0% blood, at least 2.5% blood, at least 3.0% blood, at least 3.5% blood, at least 4.0% blood, at least 4.5% blood, at least 5.0% blood, at least 5.5% blood, at least 6.0% blood, at least 6.5% blood, at least 7.0% blood, at least 7.5% blood, at least 8.0% blood, at least 8.5% blood, at least 9.0% blood, at least 9.5% blood, at least 10% blood, at least 20% blood, at least 30% blood, at least 40% blood, at least 50% blood, at least 60% blood, at least 70% blood, at least 80% blood, or at least 90% blood.

In aspects wherein the bodily fluid sample comprises urine, the urine can comprise more than 0.05% blood, more than 0.5% blood, more than 1% blood, more than 1.5% blood, more than 2.0% blood, more than 2.5% blood, more than 3.0% blood, more than 3.5% blood, more than 4.0% blood, more than 4.5% blood, more than 5.0% blood, more than 5.5% blood, more than 6.0% blood, more than 6.5% blood, more than 7.0% blood, more than 7.5% blood, more than 8.0% blood, more than 8.5% blood, more than 9.0% blood, more than 9.5% blood, more than 10% blood, more than 20% blood, more than 30% blood, more than 40% blood, more than 50% blood, more than 60% blood, more than 70% blood, more than 80% blood, or more than 90% blood.

In some aspects of any method of the present disclosure, a subject can have hematuria. Hematuria can be gross hematuria or microscopic hematuria.

A microvesicle and/or a microvesicle fraction can be isolated from a bodily fluid by any technique described herein or any suitable technique known in the art. A microvesicle and/or a microvesicle fraction can be isolated from a bodily fluid by a method comprising filtration, size exclusion chromatography, ion exchange chromatography, density gradient centrifugation, centrifugation, differential centrifugation, immunoabsorbent capture, affinity purification, affinity enrichment, affinity exclusion microfluidic separation, ultracentrifugation, nanomembrane ultrafiltration or any combination thereof.

In some aspects of any method of the present disclosure, a microvesicle or a microvesicle fraction can be isolated from a bodily fluid by a method comprising contacting the bodily fluid sample with at least one affinity agent that binds to at least one surface marker present on the surface of a microvesicle. The at least one surface marker can be selected from ADAM10, CEACAM5, CEACAM6, EPCAM, ERBB2 (HER2), FZD2, ITGA3, ITGB4, MUC1, SDC1, SLC3A2, TFRC, TNFRSF4, TNFRSF12A and TNFSF10.

In some aspects of any method of the present disclosure, a bodily fluid can be filtered prior to the isolation of at least one microvesicle or a microvesicle fraction. A bodily fluid sample can be filtered through a filter with a pore size of about 0.1 µm, or about 0.2 µm, or about 0.3 µm, or about 0.4 µm, or about 0.5 µm, or about 0.6 µm, or about 0.7 µm, or about 0.8 µm, or about 0.9 µm, or about 1.0 µm, or about 1.5 µm, or about 2.0 µm, or about 2.5 µm, or about 3.0 µm, or about 3.5 µm, or about 4.0 µm, or about 4.5 µm, or about 5.0 µm. In some aspects of any method of the present disclosure, a bodily fluid can be processed such that cells and/or cellular debris are removed prior to the isolation of at least one microvesicle or a microvesicle fraction. Pre-processing can comprise filtering, centrifugation or any combination thereof.

In some aspects of any method of the present disclosure, a predetermined cutoff value can have a positive predictive value of at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or at least 99%.

In some aspects of any method of the present disclosure, a predetermined cutoff value can have a negative predictive value of at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or at least 99%.

In some aspects of any method of the present disclosure, a predetermined cutoff value can have a sensitivity of at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or at least 99%.

In some aspects of any method of the present disclosure, a predetermined cutoff value can have a specificity of at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or at least 99%.

In some aspects of any method of the present disclosure, a subject can be at least 10 years of age, or at least 20 years of age, or at least 30 years of age, or at least 40 years of age, or at least 50 years of age, or at least 60 years of age, or at least 70 years of age, or at least 80 years of age or at least 90 years of age.

In some aspects of any method of the present disclosure, a subject can have been previously diagnosed with bladder cancer, a subject can previously have had bladder cancer, a subject can have been previously treated for bladder cancer, a subject can be suspected of having bladder cancer or any combination thereof. In some aspects of any method of the present disclosure, the subject can previously have had a radical cystectomy.

In some aspects of any method of the present disclosure, an at least one therapy can comprise performing at least one diagnostic procedure on a subject. In some aspects of any method of the present disclosure, an at least one diagnostic procedure can comprise performing a cystoscopy, performing an ultrasound, or any combination thereof.

In some aspects of any method of the present disclosure, a therapy can comprise surgery, radiation therapy, chemotherapy, intravesical therapy, anti-cancer therapy, immunotherapy, intravesical immunotherapy, targeted-drug therapy, intravesical chemotherapy or any combination thereof.

Intravesical immunotherapy can comprise the administration of at least one therapeutically effective amount of bacillus calmette-guerin.

Intravesical chemotherapy can comprise the administration of at least one therapeutically effective amount of mitomycin, the administration of at least one therapeutically effective amount of gemcitabine, the administration of at least one therapeutically effective amount of valrubicin or any combination thereof.

Surgery can comprise a transurethral resection of bladder tumor (TURBT), transurethral resection (TUR), cystectomy, a partial cystectomy, a radical cystectomy, an incontinent diversion, a continent diversion, the installation of a neo-bladder, urostomy or any combination thereof.

Chemotherapy can comprise the administration of at least one therapeutically effective amount of cisplatin, cisplatin plus fluorouracil (5-FU), mitomycin with 5-FU, a combination of gemcitabine and cisplatin, a dose-dense combination of methotrexate, vinblastine, doxorubicin (Adriamycin), and cisplatin (DDMVAC), a combination of Cisplatin, methotrexate, and vinblastine (CMV), a combination of gemcitabine and paclitaxel or any combination thereof.

Targeted drug therapy can include the administration of at least one therapeutically effective amount of a fibroblast growth factor receptor (FGFR) inhibitor. Targeted drug therapy can include the administration of at least one therapeutically effective amount of erdafitinib (balversa).

Any method of the present disclosure can comprise providing a treatment recommendation for the subject. A treatment recommendation can comprise recommending the administration of a specific therapy, recommending further diagnostic tests, recommending specific patient management steps or any combination thereof. Thus, methods described herein which include the administration of at least one therapy can instead comprise providing a treatment recommendation for the subject.

In some aspects of any method of the present disclosure, the expression level of a gene can be determined using quantitative PCR (qPCR). Quantitative PCR can be quantitative real-time PCR or semi-quantitative real-time PCR.

In some aspects of any method of the present disclosure, the expression level of a gene can be determined using reverse transcription PCR (RT-PCR).

In some aspects of any method of the present disclosure, the expression level of a gene can be determined using reverse transcription quantitative PCR (qRT-PCR).

In aspects wherein the expression level of a gene is determined using quantitative PCR, the expression level of the gene can be denoted by a cycle threshold (Ct) value.

In some aspects of the methods of the present disclosure, determining the expression level of the at least one gene and the at least one reference gene in the preceding methods comprises using quantitative reverse transcription PCR. In other aspects, determining the expression level of the at least one gene and the at least one reference gene in the preceding methods can comprise using direct detection methods. In yet another aspect, determining the expression level of the at least one gene and the at least one reference gene in the preceding methods can comprise sequencing. The sequencing can be high-throughput sequencing. In aspects comprising sequencing, the sequencing can comprise performing RNA-SEQ.

Definitions

As used herein, a "subject" or "patient" can be any mammal, e.g., a human, a primate, mouse, rat, dog, cat, cow, horse, pig, sheep, goat, camel. In a preferred aspect, the subject is a human. A subject can be diagnosed with cancer. The subject can be diagnosed with brain cancer.

The sample can be a biological sample. As will be appreciated by those in the art, the sample may comprise any number of things, including, but not limited to: cells (including both primary cells and cultured cell lines) and tissues (including cultured or explanted). In aspects, a tissue sample (fixed or unfixed) is embedded, serially sectioned, and immobilized onto a microscope slide. As is well known, a pair of serial sections will include at least one cell that is present in both serial sections. Structures and cell types, located on a first serial section will have a similar location on an adjacent serial section. The sample can be cultured cells or dissociated cells (fixed or unfixed) that have been immobilized onto a slide.

The sample can be obtained from virtually any organism including multicellular organisms, e.g., of the plant, fungus, and animal kingdoms; preferably, the sample is obtained from an animal, e.g., a mammal. Human samples are particularly preferred.

In some aspects, the preceding methods are used in the clinical assessment of a subject. As used herein the term "clinical assessment of a subject" can comprise producing a report that predicts or diagnoses a condition in a subject, determine a subject's predisposition to a condition, monitors the treatment of a condition in a subject, diagnoses a therapeutic response of a disease in a subject and prognoses the disease, disease progression, or response to particular treatment of a disease in a subject.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer or cervical cancer.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "response" or "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

The term "anti-cancer therapy" is used in the broadest sense and refers to any method known in the art for the treatment of cancer. Anti-cancer therapy can include, but is not limited to, the administration of chemotherapeutic agents, the administration of anti-cancer agents, radiation treatment, immunotherapy, surgery, radiation therapy, targeted therapy, hormone therapy and stem cell transplant. Anti-cancer therapy can comprise administering to the subject a therapeutically effective dose of at least one class of drugs. The terms "effective amount" and "therapeutically effective amount" of a drug, agent or compound of the invention is meant a nontoxic but sufficient amount of the drug, agent or compound to provide the desired effect, for example, a response or benefit in the subject.

Classes of anti-cancer agents can include, but are not limited to, antibodies.

The term "immunotherapy" can refer to activating immunotherapy or suppressing immunotherapy. As will be appreciated by those in the art, activating immunotherapy refers to the use of a therapeutic agent that induces, enhances, or promotes an immune response, including, e.g., a T cell response while suppressing immunotherapy refers to the use of a therapeutic agent that interferes with, suppresses, or inhibits an immune response, including, e.g., a T cell response. Immunotherapy can include the administration of an antibody or antibody fragment.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one aspect, the extent of binding of an anti-target antibody to an unrelated, non-target protein is less than about 10% of the binding of the antibody to target as measured, e.g., by a radioimmunoassay (RIA) or biacore assay. In certain aspects, an antibody that binds to a target has a dissociation constant (Kd) of <1 µM, <100 nM, <10 nM, <1 nM, <0.1 nM, <0.01 nM, or <0.001 nM (e.g. $10^8$ M or less, e.g. from $10^8$ M to $10^{13}$ M, e.g., from $10^9$ M to $10^{13}$ M). In certain aspects, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some aspects, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Classes of anti-cancer or chemotherapeutic agents can include alkylating agents, platinum agents, taxanes, *vinca* agents, anti-estrogen drugs, aromatase inhibitors, ovarian suppression agents, endocrine/hormonal agents, bisphophonate therapy agents and targeted biological therapy agents.

Specific anti-cancer or chemotherapeutic agents can include cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb or bevacizumab, or combinations thereof.

Combinational anti-cancer or chemotherapeutic therapies can include AT: Adriamycin® (Doxorubicin) and Taxotere® (Docetaxel); AC: Adriamycin®, Cytoxan® (Cyclophosphamide); AC+Taxol®; AC+Taxotere®; CMF: Cytoxan®, Methotrexate, 5-fluorouracil; CEF: Cytoxan®, Ellence® (Epirubicin), and fluorouracil; EC: Ellence®, Cytoxan®; FAC: 5-fluorouracil, Adriamycin®, and Cytoxan®; GET: Gemzar® (Gemcitabine), Ellence®, and Taxol®; TC: Taxotere®, Cytoxan®; TC: Taxotere®, Paraplatin® (Carboplatin); TAC: Taxotere®, Adriamycin®, Cytoxan® or TCH: Taxotere®, Herceptin® (Trastuzumab), and Paraplatin®. Additional combination chemotherapeutic therapies for cancer can include: Taxol® and Xeloda® (Capecitabine); Taxotere® and Xeloda®; Taxotere® and Paraplatin®; Taxol® and Paraplatin®; Taxol® and Gemzar®; Abraxane® (Protein-bound Paclitaxel) and Xeloda®; Abraxane® and Paraplatin®; Camptosor® (Irinotecan) and Temodar® (Temozolomide); Gemzar® and Paraplatin® or Ixempra® (Ixabepilone) and Xeloda®

As used herein, "treating" or "treat" describes the management and care of a patient for the purpose of combating a disease, condition, or disorder and includes, but is not limited to, the administration of chemotherapy, immunotherapy, radiotherapy, or a combination thereof, to alleviate the symptoms or complications of a disease, condition or disorder, or to eliminate the disease, condition or disorder.

As used herein, the term "alleviating" or "alleviate" is meant to describe a process by which the severity of a sign or symptom of a disorder is decreased. Importantly, a sign or symptom can be alleviated without being eliminated.

A chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

General Methods

Determining Gene Expression Levels

In methods of the present disclosure, expression levels of genes can be measured using any methods known in the art. These methods include, but are not limited to sequencing, direct detection, and amplification-based methods.

In aspects with direct detections methods, the extracted nucleic acids, including DNA and/or RNA, are analyzed directly without an amplification step. Direct analysis may be performed with different methods including, but not limited to, the NanoString technology. NanoString technology enables identification and quantification of individual target molecules in a biological sample by attaching a color coded fluorescent reporter to each target molecule. These methods are described in Geiss et al. (see Geiss et al. *Nature Biotechnology*, 2008, 26 (3): 317-325), which is incorporated herein by reference.

In other aspects, it may be beneficial or otherwise desirable to amplify the nucleic acid of the microvesicle prior to analyzing it. Methods of nucleic acid amplification are commonly used and generally known in the art. If desired, the amplification can be performed such that it is quantitative. Quantitative amplification will allow quantitative determination of relative amounts of the various nucleic acids, to generate a profile.

In one embodiment, the extracted nucleic acid is RNA. RNA molecules are then preferably reverse-transcribed into complementary DNAs before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods.

The analysis of nucleic acids present in the microvesicles is quantitative and/or qualitative. For quantitative analysis, the amounts (expression levels), either relative or absolute, of specific nucleic acids of interest within the microvesicles are measured with methods known in the art (described below). For qualitative analysis, the species of specific nucleic acids of interest within the microvesicles, whether wild type or variants, are identified with methods known in the art (described below).

Sequencing methods can include, but are not limited to RNA-seq. In some aspects, RNA-seq comprises reverse transcribing at least one RNA molecule to produce at least one double-stranded complementary DNA molecule (dscDNA). Methods known in the art for creating a dscDNA library may be used. RNA-seq can further comprise appending sequencing adaptors to the at least one dscDNA molecule, followed by amplification, and finally sequencing. Methods of sequencing known in the art, including sequencing by synthesis can be used. The various RNA-seq methods known in the art may be used. Base abundances obtained using RNA-seq methods can be measured as read counts and normalized using methods known in the art (e.g. Love, M I, Huber W, and Anders, S, "Moderated estimation of fold change and dispersion for RNA-seq data with DESeq2", *Genome Biology*, 2015 15:500, herein incorporated by reference). Gene abundances can also be reported in Reads Per Million (RPM) or Transcripts Per Million (TPM).

In some aspects, "next-generation" sequencing (NGS) or high-throughput sequencing experiments are performed. These sequencing techniques allow for the identification of nucleic acids present in low or high abundance in a sample, or which are otherwise not detected by more conventional hybridization methods or a quantitative PCR method. NGS typically incorporates the addition of nucleotides followed by washing steps.

Commercially available kits for total RNA SEQUENCING which preserves the strand information, meant for mammalian RNA and very low input RNA are useful in this regard, and include, without limitation, Clontech: SMARTer stranded total RNASeq kit; Clontech: SMARTSeq v4 ultra low input RNASeq kit; Illumina: Truseq stranded total RNA library prep kit; Kapa Biosystems: Kapa stranded RNASeq library preparation kit; New England Biolabs: NEBNext ultra directional library prep kit; Nugen: Ovation Solo RNASeq kit; and Nugen: Nugen Ovation RNASeq system v2.

The methods of the present disclosure can use reference genes to normalize the measured abundance of other genes and biomarkers. Normalization can be used to control for experimental variation to facilitate more accurate comparisons between measurements from different samples. In a non-limiting example, a first sample from a first patient and a second sample from a second patient are analyzed. The first sample from the first patient may be more concentrated than the second sample from the second patient, meaning more nucleic acids are extracted from the first sample than are extracted from the second sample. Thus, if the expression level of a particular gene is measured in the two samples, the expression level of the gene will appear higher in the first sample than the second sample, simply because there are more nucleic acid molecule in the first sample. To more accurately compare between the two samples, the two measured expression levels can be normalized.

Normalization can also be used to control for unwanted biological variation. In a non-limiting example, biological variation can result from some feature of the patient or the sample collection that is not relevant to the methods of the present disclosure, such as blood-exosome concentration due to high or low blood pressure, variations created by collecting samples at different times of the day and variation to due patient age or patient sex.

In methods of the present disclosure, the measured expression level of a particular gene can be normalized using methods known in the art. In a non-limiting example, normalization can be achieved by dividing the measured expression level of a gene of interest by a reference gene. Useful reference genes are genes that show a low variation in their expression level across a variety of different samples and patients. For example, a useful reference gene will show the same expression level in samples derived from subjects who have cancer and in samples derived from subjects who do not have cancer. In another example, a useful reference gene will show the same expression level in samples derived from a subject with cancer before treatment with an anti-cancer therapy and in in samples derived from a subject with cancer after treatment with an anti-cancer therapy. The variation in expression level can be quantified by different methods known in the art. For example, the variation in expression level of a gene can be quantified by calculating the coefficient of variation in the expression level of a particular gene across a set of different samples.

Isolation of Microvesicles

Several methods of isolating microvesicles from a biological sample have been described in the art. For example, a method of differential centrifugation is described in a paper by Raposo et al. (Raposo et al., 1996), a paper by Skog et. al. (Skog et al., 2008) and a paper by Nilsson et. al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al. (Miranda et al., 2010). Further, microvesicles may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner.

In some aspects, the sample isolation and analysis techniques encompass the methods referred to as EXO50 and/or EXO52 as described in, e.g., WO 2014/107571 and WO 2016/007755, each incorporated by reference herein in the entirety. Also contemplated are the commercially available liquid biopsy platforms sold under the trademarks EXOLUTION™, EXOLUTION PLUS™, EXOLUTION™ UPREP, EXOLUTION HT™ UPREP™, EXOEASY™, EXORNEASY™, each available from Exosome Diagnostics, Inc., as well as the QIAamp Circulating Nucleic Acids Kit, DNeasy Blood & Tissue Kits, AllPrep DNA/RNA Mini Kit, and the AllPrep DNA/RNA/Protein Mini Kit, each available from Qiagen.

The isolation methods for exosomes for the further purification of extracellular vesicles having associated nucleic acids described herein also include: 1) Ultracentrifugation, often in combination with sucrose density gradients or sucrose cushions to float the relatively low-density exosomes. Isolation of exosomes by sequential differential centrifugations, combined with sucrose gradient ultracentrifugation, can provide high enrichment of exosomes. 2) The use of volume-excluding polymer selected from the group consisting of polyethylene glycol, dextran, dextran sulfate, dextran acetate, polyvinyl alcohol, polyvinyl acetate, or polyvinyl sulfate; and wherein the molecular weight of the volume-excluding polymer is from 1000 to 35000 daltons performed in conjunction with the additive sodium chloride from 0-1M. 3) Size exclusion chromatography, for example, Sephadex™ G200 column matrix. 4) Selective immunoaffinity or charge-based capture using paramagnetic beads (including immuno-precipitation), for example, by using antibodies directed against the surface antigens including but not limited to EpCAM, CD326, KSA, TROP1. The selection antibodies can be conjugated to paramagnetic microbeads. 5) Direct precipitation with chaotropic agents such as guanidinium thiocyanate.

Isolation of microvesicles can be achieved via a membrane as the capture surface, although it should be understood that the format of the capturing surface, e.g., beads or a filter (also referred to herein as a membrane), does not affect the ability of the methods provided herein to efficiently capture extracellular vesicles from a biological sample.

In aspects where the capture surface is a membrane, the device for isolating the extracellular vesicle fraction from a biological sample contains at least one membrane. In some aspects, the device comprises one, two, three, four, five or six membranes. In some aspects, the device comprises three membranes. In aspects where the device comprises more than one membrane, the membranes are all directly adjacent to one another at one end of the column. In aspects where the device comprises more than one membrane, the membranes are all identical to each other, i.e., are of the same charge and/or have the same functional group.

It should be noted that capture by filtering through a pore size smaller than the extracellular vesicles is not the primary mechanism of capture by the methods provided herein. However, filter pore size is nevertheless very important, e.g. because mRNA gets stuck on a 20 nm filter and cannot be recovered, whereas microRNAs can easily be eluted off, and e.g. because the filter pore size is an important parameter in available surface capture area.

The methods provided herein use samples isolated by any of a variety of capture surfaces. In some aspects, the capture surface is a membrane, also referred to herein as a filter or a membrane filter. In some aspects, the capture surface is a commercially available membrane. In some aspects, the capture surface is a charged commercially available membrane. In some aspects, the capture surface is neutral. In some aspects, the capture surface is selected from Mustang® Ion Exchange Membrane from PALL Corporation; Vivapure® Q membrane from Sartorius AG; Sartobind Q, or Vivapure® Q Maxi H; Sartobind® D from Sartorius AG, Sartobind(S) from Sartorius AG, Sartobind® Q from Sartorius AG, Sartobind® IDA from Sartorius AG, Sartobind® Aldehyde from Sartorius AG, Whatman® DE81 from Sigma, Fast Trap Virus Purification column from EMD Millipore; Thermo Scientific* Pierce Strong Cation and Anion Exchange Spin Columns.

In aspects where the capture surface is charged, the capture surface can be a charged filter selected from the group consisting of 0.65 µm positively charged Q PES vacuum filtration (Millipore), 3-5 µm positively charged Q RC spin column filtration (Sartorius), 0.8 µm positively charged Q PES homemade spin column filtration (Pall), 0.8 µm positively charged Q PES syringe filtration (Pall), 0.8 µm negatively charged S PES homemade spin column filtration (Pall), 0.8 µm negatively charged S PES syringe filtration (Pall), and 50 nm negatively charged nylon syringe filtration (Sterlitech). In some aspects, the charged filter is not housed in a syringe filtration apparatus, as nucleic acid can be harder to get out of the filter in these aspects. In some aspects, the charged filter is housed at one end of a column.

In aspects where the capture surface is a membrane, the membrane can be made from a variety of suitable materials. In some aspects, the membrane is polyethersulfone (PES) (e.g., from Millipore or PALL Corp.). In some aspects, the membrane is regenerated cellulose (RC) (e.g., from Sartorius or Pierce).

In some aspects, the capture surface is a positively charged membrane. In some aspects, the capture surface is a Q membrane, which is a positively charged membrane and is an anion exchanger with quaternary amines. For example, the Q membrane is functionalized with quaternary ammonium, $R-CH_2-N^+(CH_3)_3$. In some aspects, the capture surface is a negatively charged membrane. In some aspects, the capture surface is an S membrane, which is a negatively charged membrane and is a cation exchanger with sulfonic acid groups. For example, the S membrane is functionalized with sulfonic acid, $R-CH_2-SO_3^-$. In some aspects, the capture surface is a D membrane, which is a weak basic anion exchanger with diethylamine groups, $R-CH_2-NH^+(C_2H_5)_2$. In some aspects, the capture surface is a metal chelate membrane. For example, the membrane is an IDA membrane, functionalized with minodiacetic acid $-N(CH_2COOH^-)_2$. In some aspects, the capture surface is a microporous membrane, functionalized with aldehyde groups, $-CHO$. In other aspects, the membrane is a weak basic anion exchanger, with diethylaminoethyl (DEAE) cellulose. Not all charged membranes are suitable for use in the methods provided herein, e.g., RNA isolated using Sartorius Vivapure S membrane spin column showed RT-qPCR inhibition and, thus, unsuitable for PCR related downstream assay.

In aspects where the capture surface is charged, extracellular vesicles can be isolated with a positively charged filter.

In aspects where the capture surface is charged, the pH during extracellular vesicle capture is a pH≤7. In some aspects, the pH is greater than 4 and less than or equal to 8.

In aspects where the capture surface is a positively charged Q filter, the buffer system includes a wash buffer comprising 250 mM Bis Tris Propane, pH 6.5-7.0. In aspects where the capture surface is a positively charged Q filter, the lysis buffer is a GTC-based reagent. In aspects where the capture surface is a positively charged Q filter, the lysis buffer is present at one volume. In aspects where the capture surface is a positively charged Q filter, the lysis buffer is present at more than one volume.

Depending on the membrane material, the pore sizes of the membrane range from 3 µm to 20 nm. For example, in aspects where the capture surface is a commercially available PES membrane, the membrane has a pore size of 20 nm (Exomir), 0.65 µm (Millipore) or 0.8 µm (Pall). In aspects where the capture surface is a commercially available RC membrane, the membrane has a pore size in the range of 3-5 µm (Sartorius, Pierce).

The surface charge of the capture surface can be positive, negative or neutral. In some aspects, the capture surface is a positively charged bead or beads.

In some aspects, the sample is not pre-processed prior to isolation of microvesicles and extraction of nucleic acids, e.g., DNA and/or DNA and RNA, from the biological sample.

In some aspects, the sample is subjected to a pre-processing step prior to isolation, purification or enrichment of the extracellular vesicles is performed to remove large unwanted particles, cells and/or cell debris and other contaminants present in the biological sample. The pre-processing steps may be achieved through one or more centrifugation steps (e.g., differential centrifugation) or one or more filtration steps (e.g., ultrafiltration), or a combination thereof.

Where more than one centrifugation pre-processing steps are performed, the biological sample may be centrifuged first at the lower speed and then at the higher speed. If desired, further suitable centrifugation pre-processing steps may be carried out. Alternatively, or in addition to the one or more centrifugation pre-processing steps, the biological sample may be filtered. For example, a biological sample may be first centrifuged at 20,000 g for 1 hour to remove large unwanted particles; the sample can then be filtered, for example, through a 0.8 µm filter.

In some aspects, the sample is pre-filtered to exclude particles larger than 0.8 µm. In some aspects, the sample includes an additive such as EDTA, sodium citrate, and/or citrate-phosphate-dextrose. In some aspects, the sample does not contain heparin, as heparin can negatively impact RT-qPCR and other nucleic acid analysis. In some aspects, the sample is mixed with a buffer prior to purification and/or nucleic acid isolation and/or extraction. In some aspects, the buffer is a binding buffer.

In some aspects, one or more centrifugation steps are performed before or after contacting the biological sample with the capture surface to separate extracellular vesicles and concentrate the extracellular vesicles isolated from the biological fraction. To remove large unwanted particles, cells, and/or cell debris, the samples may be centrifuged at a low speed of about 100-500 g, for example, in some aspects, about 250-300 g. Alternatively or in addition, the samples may be centrifuged at a higher speed. Suitable centrifugation speeds are up to about 200,000 g; for example, from about 2,000 g to less than about 200,000 g. Speeds of above about 15,000 g and less than about 200,000 g or above about 15,000 g and less than about 100,000 g or above about 15,000 g and less than about 50,000 g are used in some aspects. Speeds of from about 18,000 g to about 40,000 g or about 30,000 g; and from about 18,000 g to about 25,000 g are more preferred. In some aspects, a centrifugation speed of about 20,000 g. Generally, suitable times for centrifugation are from about 5 minutes to about 2 hours, for example, from about 10 minutes to about 1.5 hours, or for about 15 minutes to about 1 hour. A time of about 0.5 hours may be used. It is sometimes useful, in some aspects, to subject the biological sample to centrifugation at about 20,000 g for about 0.5 hours. However, the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., for example, about 1-5° C., e.g., about 3° C. or about 4° C.

In some aspects, one or more filtration steps are performed before or after contacting the biological sample with the capture surface. A filter having a size in the range about 0.1 to about 1.0 µm may be employed, for example, about 0.8 µm or 0.22 µm. The filtration may also be performed with successive filtrations using filters with decreasing porosity.

In some aspects, one or more concentration steps are performed, in order to reduce the volumes of sample to be treated during the chromatography stages, before or after contacting the biological sample with the capture surface. Concentration may be through centrifugation of the sample at high speeds, e.g. between 10,000 and 100,000 g, to cause the sedimentation of the extracellular vesicles. This may consist of a series of differential centrifugations. The extracellular vesicles in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the extracellular vesicle fraction. In another embodiment, the filtration is an ultrafiltration, for example, a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibers (Amicon, Millipore, Sartorius, Pall, GF, Sepracor). Within the scope of the invention, the use of membranes with a cut-off threshold below 1000 kDa, for example, in some aspects, between 100 kDa and 1000 kDa, or for example, in some aspects, between 100 kDa and 600 kDa, is advantageous.

In some aspects, one or more size-exclusion chromatography step or gel permeation chromatography steps are performed before or after contacting the biological sample with the capture surface. To perform the gel permeation chromatography step, a support selected from silica, acrylamide, agarose, dextran, ethylene glycol-methacrylate co-polymer or mixtures thereof, e.g., agarose-dextran mixtures, are used in some aspects. For example, such supports include, but are not limited to: SUPERDEX® 200 HR (Pharmacia), TSK G6000 (TosoHaas) or SEPHACRYL® S (Pharmacia).

In some aspects, one or more affinity chromatography steps are performed before or after contacting the biological sample with the capture surface. Some extracellular vesicles can also be characterized by certain surface molecules. Because microvesicles form from budding of the cell plasma membrane, these microvesicles often share many of the same surface molecules found on the cells they originated from. As used herein, "surface molecules" refers collectively to antigens, proteins, lipids, carbohydrates, and markers found on the surface or in or on the membrane of the microvesicle. These surface molecules can include, for example, receptors, tumor-associated antigens, membrane protein modifications (e.g., glycosylated structures). For example, microvesicles that bud from tumor cells often display tumor-associated antigens on their cell surface. As such, affinity chromatography or affinity exclusion chromatography can also be utilized in combination with the methods provided herein to isolate, identify, and or enrich for specific populations of microvesicles from a specific donor cell type (Al-Nedawi et al., 2008; Taylor and Gercel-Taylor, 2008). For example, tumor (malignant or non-malignant) microvesicles carry tumor-associated surface antigens and may be detected, isolated and/or enriched via these specific tumor-associated surface antigens. In one example, the surface antigen is epithelial cell adhesion molecule (EpCAM), which is specific to microvesicles from carcinomas of lung, colorectal, breast, prostate, head and neck, and hepatic origin, but not of hematological cell origin (Balzar et al., 1999; Went et al., 2004). Additionally, tumor-specific microvesicles can also be characterized by the lack of certain surface markers, such as CD80 and CD86. In these cases, microvesicles with these markers may be excluded for further analysis of tumor specific markers, e.g., by affinity exclusion chromatography. Affinity chromatography can be accomplished, for example, by using different supports, resins, beads, antibodies, aptamers, aptamer analogs, molecularly imprinted polymers, or other molecules known in the art that specifically target desired surface molecules on microvesicles.

Extraction of Nucleic Acids

Following the isolation of extracellular vesicles from a biological sample, nucleic acid may be extracted from the isolated or enriched extracellular vesicle fraction. To achieve this, the extracellular vesicles may first be lysed. The lysis of extracellular vesicles and extraction of nucleic acids may be achieved with various methods known in the art, including those described in PCT Publication Nos. WO 2016/007755 and WO 2014/107571, the contents of each of which are hereby incorporated by reference in their entirety. Nucleic acid extraction may be achieved using protein precipitation according to standard procedures and techniques known in the art. Such methods may also utilize a nucleic acid-binding column to capture the nucleic acids contained within the extracellular vesicles. Once bound, the nucleic acids can then be eluted using a buffer or solution suitable to disrupt the interaction between the nucleic acids and the binding column, thereby eluting the nucleic acids.

Exosomal derived nucleic acids can include RNA or DNA, either individually or as a mixture of RNA and DNA. Exosomal derived nucleic acids can include material either contained within or bound to the outer surface of exosomes. The DNA component can be exosomal or other cell-free sources (cfDNA).

Where an extracellular vesicle fraction is utilized, isolation and extraction of nucleic acids, e.g., DNA and/or DNA and nucleic acids including at least RNA from a sample using the following general procedure. First, the nucleic acids in the sample, e.g., the DNA and/or the DNA and the extracellular vesicle fraction, are bound to a capture surface such as a membrane filter, and the capture surface is washed. Then, an elution reagent is used to perform on-membrane lysis and release of the nucleic acids, e.g., DNA and/or DNA and RNA, thereby forming an eluate. The eluate is then contacted with a protein precipitation buffer that includes a transition metal and a buffering agent. The cfDNA and/or DNA and nucleic acids include at least the RNA from the extracellular vesicles is then isolated from the protein-precipitated eluate using any of a variety of art-recognized techniques, such as, for example, binding to a silica column followed by washing and elution.

The elution buffer may comprise a denaturing agent, a detergent, a buffer substance, and/or combinations thereof to maintain a defined solution pH. The elution buffer may include a strong denaturing agent, or even a strong denaturing agent and a reduction agent.

In some aspects, one or more control particles or one or more nucleic acid(s) may be added to the sample prior to extracellular vesicle isolation and/or nucleic acid extraction to serve as an internal control to evaluate the efficiency or quality of extracellular vesicle purification and/or nucleic acid extraction. The methods described herein provide for the efficient isolation and the control nucleic acid(s) along with the extracellular vesicle fraction. These control nucleic acid(s) include one or more nucleic acids from Q-beta bacteriophage, one or more nucleic acids from virus particles, or any other control nucleic acids (e.g., at least one control target gene) that may be naturally occurring or engineered by recombinant DNA techniques. In some aspects, the quantity of control nucleic acid(s) is known before the addition to the sample. The control target gene can be quantified using real-time PCR analysis. Quantification of a control target gene can be used to determine the efficiency or quality of the extracellular vesicle purification or nucleic acid extraction processes.

In some aspects, the control nucleic acid is a nucleic acid from a Q-beta bacteriophage, referred to herein as "Q-beta control nucleic acid." The Q-beta control nucleic acid used in the methods described herein may be a naturally-occurring virus control nucleic acid or may be a recombinant or engineered control nucleic acid. Q-beta is a member of the leviviridae family, characterized by a linear, single-stranded RNA genome that consists of 3 genes encoding four viral proteins: a coat protein, a maturation protein, a lysis protein, and RNA replicase. When the Q-beta particle itself is used as a control, due to its similar size to average microvesicles, Q-beta can be easily purified from a biological sample using the same purification methods used to isolate microvesicles, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. When the Q-beta particle itself is used as a control, after addition of the Q-beta particles to the biological sample, the nucleic acids from the Q-beta particle are extracted along with the nucleic acids from the biological sample using the extraction methods described herein. When a nucleic acid from Q-beta, for example, RNA from Q-beta, is used as a control, the Q-beta nucleic acid is extracted along with the nucleic acids from the biological sample using the extraction methods described herein. Detection of the Q-beta control target gene can be determined by RT-PCR analysis, for example, simultaneously with the biomarker(s) of interest. A standard curve of at least 2, 3, or 4 known concentrations in 10-fold dilution of a control target gene can be used to determine copy number. The copy number detected and the quantity of Q-beta particle added or the copy number detected and the quantity of Q-beta nucleic acid, for example, Q-beta RNA, added can be compared to determine the quality of the isolation and/or extraction process.

In some aspects, 50, 100, 150, 200, 250, 300, 350, 400, 450, 500, 1,000 or 5,000 copies of Q-beta particles or Q-beta nucleic acid, for example, Q-beta RNA, added to a bodily fluid sample. In some aspects, 100 copies of Q-beta particles or Q-beta nucleic acid, for example, Q-beta RNA, are added to a bodily fluid sample. When the Q-beta particle itself is used as control, the copy number of Q-beta particles can be calculated based on the ability of the Q-beta bacteriophage to infect target cells. Thus, the copy number of Q-beta particles is correlated to the colony forming units of the Q-beta bacteriophage.

Optionally, control particles may be added to the sample prior to extracellular vesicle isolation or nucleic acid extraction to serve as an internal control to evaluate the efficiency or quality of extracellular vesicle purification and/or nucleic acid extraction. The methods described herein provide for the efficient isolation and the control particles along with the extracellular vesicle fraction. These control particles include Q-beta bacteriophage, virus particles, or any other particle that contains control nucleic acids (e.g., at least one control target gene) that may be naturally occurring or engineered by recombinant DNA techniques. In some aspects, the quantity of control particles is known before the addition to the sample. The control target gene can be quantified using real-time PCR analysis. Quantification of a control target gene can be used to determine the efficiency or quality of the extracellular vesicle purification or nucleic acid extraction processes.

In some aspects, the Q-beta particles are added to the urine sample prior to nucleic extraction. For example, the Q-beta particles are added to the urine sample prior to ultrafiltration and/or after the pre-filtration step.

In some aspects, the methods and kits described herein include one or more in-process controls. In some aspects, the in-process control is detection and analysis of a reference gene that indicates sample quality (i.e., an indicator of the quality of the biological sample, e.g., biofluid sample). In some aspects, the in-process control is detection and analysis of a reference gene that indicates plasma quality (i.e., an indicator of the quality of the plasma sample). In some aspects, the reference gene(s) is/are analyzed by additional qPCR.

In some aspects, the in-process control is an in-process control for reverse transcriptase and/or PCR performance. These in-process controls include, by way of non-limiting examples, a reference RNA (also referred to herein as ref.RNA), that is spiked in after RNA isolation and prior to reverse transcription. In some aspects, the ref.RNA is a control such as Qbeta. In some aspects, the ref.RNA is analyzed by additional PCR.

In some aspects, a spike-in of synthetic RNA or DNA standard, also referred to herein as a "synthetic spike-in" is included as a quality control metric, or at any step prior to sequencing library preparation. Exogenous materials such as synthetic nucleic acids, can serve as sample quality control reagents, quantification reagents, can enable limit of detection, dynamic range and technical reproducibility studies and/or can enable studies detecting particular sequences.

Commercially available synthetic spike-ins include, without limitation, Dharmacon: Solaris RNA spike-in control kit; Exiqon: RNA spike-in kit; Horizon Diagnostics: Reference standards, Lexogen: spike-in RNA variant control mixes; Thermo Fisher Scientific: ERCC RNA spike-in control mixes; and Qbeta RNA spike-in, yeast or *Arabidopsis* RNA.

In some aspects, the synthetic spike-in is added to the sample at different dilutions. In some aspects, the dilution of the spike-ins to be added to the sample can be in the range of 1:1000 to 1:10,000,000, including, without limitation, dilutions of 1:1000, 1:10,000, 1:100,000, 1:1,000,000 and even 1:10,000,000. The specific dilution of spike-ins to be added to the sample is determined based on the quantity and/or the quality and/or source of the nucleic acids present in the sample.

In some aspects, the sample can either be subjected to a reverse transcription reaction or untreated. The RNA within a sample is reverse transcribed when it is of interest to convert the RNA to cDNA. In some aspects, only first stand synthesis is conducted when only single stranded cDNA is desired. In some aspects, both first strand and second strand synthesis is conducted when double stranded DNA is desired. In some aspects, the sample is untreated when it is of interest to only investigate DNA fractions within the sample. In some aspects, the cDNA processing steps include, for example but not limited to retaining strand information by treating with uracil-N-glycosylase and/or by orientation of NGS adapter sequences, cleavage of RNA, fragmentation of RNA, incorporation of non-canonical nucleotides, annealing or ligation of adapter sequences (adaptor ligation), second strand synthesis, etc.

In some aspects, the sample is subjected to fragmentation or untreated. Fragmentation can be achieved using enzymatic or non-enzymatic processes or by physical shearing of the material with RNA or dsDNA. In some aspects, fragmentation of the RNA and/or dsDNA is conducted by heat denaturation in the presence of divalent cations. The specific duration of fragmentation time of the sample is determined based on the quantity and/or the quality and/or source of the nucleic acids present in the sample. In some aspects, the duration of fragmentation time ranges from 0 minute to 30 minutes.

In some aspects, sequencing adaptors are added to the material using ligation based approaches following end-repair and adenylation, such as polyadenylation. In some aspects, sequencing adaptors are added to the material using PCR-based approaches. Nucleic acids within the sample, which have gone through any of the aspects described above and now have sequence adaptors will hereto be described as 'library' when referring to the entire collection of nucleic acid fragments within the sample or 'library fragment' when referring to the fragment of nucleic acid that has been incorporated within the context of the sequence adaptors. Inclusion of unique molecular index (UMI), unique identifier, or molecular tag in the adapter sequence provides an added benefit for read de-duplication and enhanced estimation of the input number of nucleic acid molecules in the sample.

In some aspects, using bead-based separation techniques, the library can be subjected to a process whereby composition of the library can be further modified to: 1) remove unwanted products (including but not restricted to; residual adaptors, primers, buffers, enzymes, adaptor dimers); 2) be of a certain size range (by altering the bead or bead buffer reagent to sample ratio, low and/or high molecular weight products can be either included or excluded in the sample); 3) concentrate the sample by elution in minimal volume. This process is commonly referred to as a 'clean up' step or the sample is 'cleaned up' and will hereto be referred to as such. Bead-based separation techniques can include but are not limited to paramagnetic beads. Bead-based clean up can be conducted once or multiple times if required or desired.

Commercially available paramagnetic beads useful according to the methods herein include, without limitation, Beckman Coulter: Agencourt AMPure XP; Beckman Coulter: Agencourt RNAclean XP; Kapa Biosystems: Kapa Pure beads; Omega Biosystems: MagBind TotalPure NGS beads; and ThermoFisher Scientific: Dynabeads.

Following bead-based clean up, the library can be amplified en masse using universal primers that target the adaptor sequence. The number of amplification cycles can be modified to produce enough product that is required for downstream processing steps.

Library quantity and quality is quantified using, but not limited to, fluorometric techniques such as Qubit dsDNA HS assay and/or Agilent Bioanalyzer HS DNA assay. The libraries can then be normalized, multiplexed and subjected to sequencing on any next generation sequencing platform.

In some aspects, the extracted nucleic acid comprises DNA and/or DNA and RNA. In aspects where the extracted nucleic acid comprises DNA and RNA, the RNA is reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR. As demonstrated in the examples that follow, the RNAs extracted from nucleic acid-containing particles using the methods disclosed herein include many species of transcripts including, but not limited to, ribosomal 18S and 28S rRNA, microRNAs, transfer RNAs, transcripts that are associated with diseases or medical conditions, and biomarkers that are important for diagnosis, prognosis and monitoring of medical conditions.

For example, RT-PCR analysis determines a Ct (cycle threshold) value for each reaction. In RT-PCR, a positive reaction is detected by accumulation of a fluorescence signal. The Ct value is defined as the number of cycles required for the fluorescent signal to cross the threshold (i.e., exceeds background level). Ct values are inversely proportional to the amount of target nucleic acid, or control nucleic acid, in the sample (i.e., the lower the Ct value, the greater the amount of control nucleic acid in the sample).

In another aspect, the copy number of the control nucleic acid can be measured using any of a variety of art-recognized techniques, including, but not limited to, RT-PCR. Copy number of the control nucleic acid can be determined using methods known in the art, such as by generating and utilizing a calibration, or standard curve.

Any of the above aspects and embodiments can be combined with any other aspect or embodiment as disclosed here in the Summary and/or Detailed Description sections.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present disclosure, the preferred materials and methods are described herein. It is to be understood that the terminology used herein is for the purpose of describing particular aspects only, and is not intended to be limiting.

EXAMPLES

Example 1

To determine urinary biomarkers for use in a urinary microvesicle-based bladder cancer screening, the following method was used.

In a first step, potential biomarkers were selected by identifying genes that were differentially expressed in the tumor tissues of interest (i.e. bladder cancer tumors). RNA expression data from databases such as the Cancer Genome Atlas were analyzed to find genes, for example, that displayed a fold-change in cancer vs healthy patients of greater than or equal to 2. Specifically, RNA expression data from the bladder, kidney, prostate and testis were analyzed.

In a second step, the potential biomarkers identified in step one were then further analyzed to determine if in healthy patients, these genes were primarily expressed only in the tissues of interest, namely the bladder, kidney, prostate or testis. The target was to have greater than or equal to 80% of the signal from each biomarker originate from one of these tissues as compared to other, contaminating tissues.

In an optional third step, the remaining biomarkers were analyzed to see if they are detected in microvesicular nucleic acid isolated from blood, urine and CSF that had been analyzed using RNA sequencing. The relative fraction of each gene contributed by each biofluid could be estimated to help to control for the contamination from off-target biofluids.

The results of this analysis are shown in FIG. 1. FIG. 1 shows that 15 genes, DHRS2, UPK2, UPK1A, KRT20, UPK1B, ACER2, SNX31, VGLL1, FER1L4, UPK3A, OSR1, GATA3, SCUBE2, GAPDH, ADAM15 were identified as potential biomarkers for use in bladder cancer screening using urinary microvesicles. HBB is also shown in FIG. 1 as it can be measured to determine the amount of blood in a urine sample from a patient.

In FIG. 1, the bladder cancer fraction denotes the percentage of expression signal of that gene that originates from bladder tissue. The urine fraction is the percentage of the signal of that gene that originates from urinary microvesicles as compared to blood and CSF. The acronym TPM in FIG. 1 denotes transcripts per million.

In another experiment, the RNA-seq signal and qPCR signal for each of the 15 candidate biomarkers were analyzed to determine if the two signals were well correlated. For the RNA-seq experiments, healthy (non-bladder cancer) urinary microvesicles were isolated by size exclusion and filtering through a 0.8 μm filter. The RNA was then extracted from these microvesicles and analyzed using RNA-seq. For the qPCR experiments, exosomal RNA was extracted from urinary microvesicles that had been isolated from two healthy urine samples using ion-exchange chromatography. The extracted exosomal RNA was then analyzed using qPCR. The RNA-seq and qPCR data were compared, and the two datasets exhibited concordance, as shown in FIG. 2.

Figure 3:
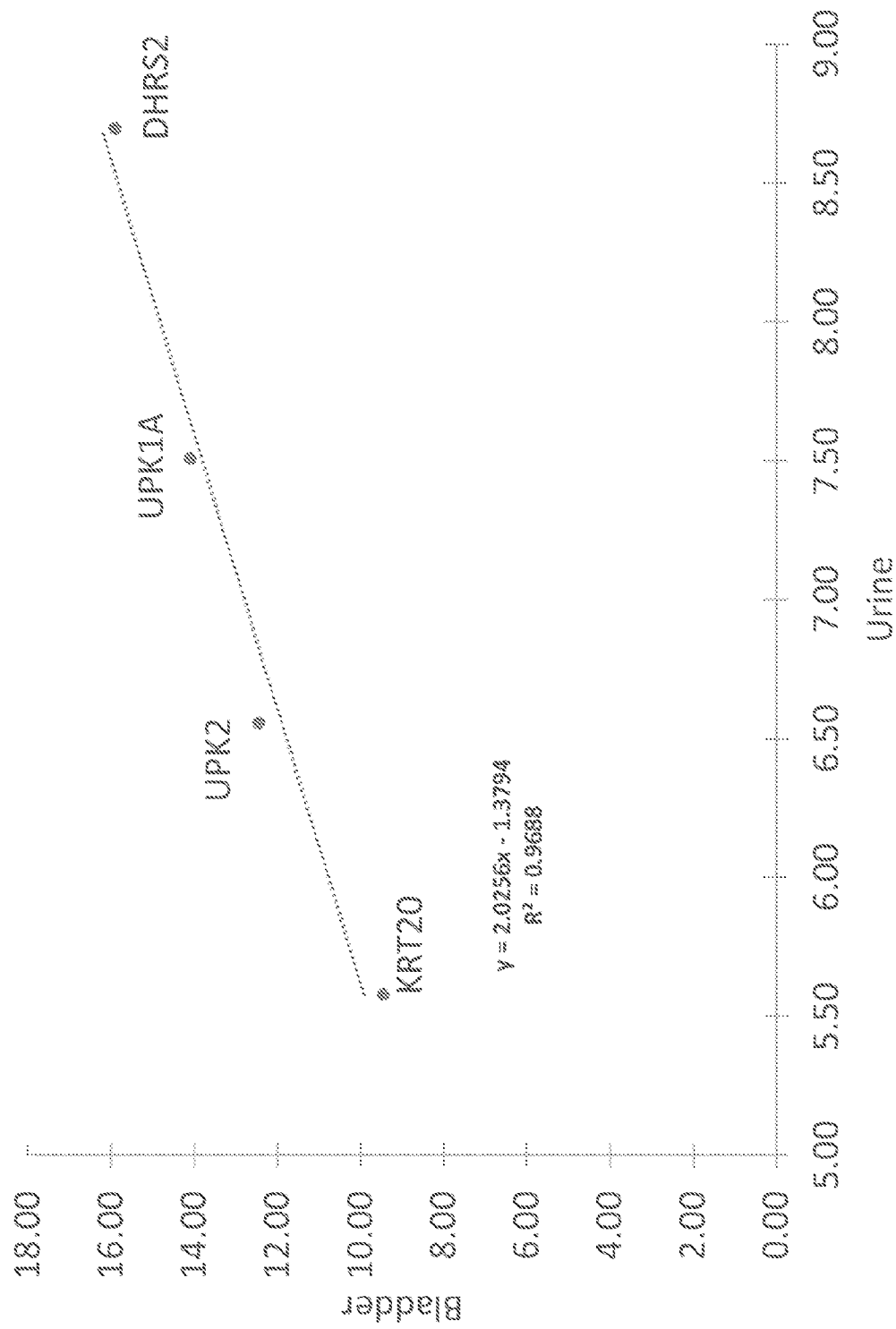
FIG. 3 is a graph showing a comparison of the expression levels of four biomarkers of the present disclosure measured in bladder tissue (y-axis) or in urinary microvesicles (x-axis).

For the top bladder-specific genes, DHRS2, UPK2, UPK1A and KRT20, RNA-seq data from bladder tissue and urinary microvesicles were compared, as shown in FIG. 3. The two datasets exhibited concordance, indicating that the detection of the expression level of these four genes in urinary microvesicles is similar to the expression level of these four genes in bladder tissues. Thus, the expression level in urinary microvesicles can be used as a proxy for the expression in bladder tissue.

Example 2

Figure 4:
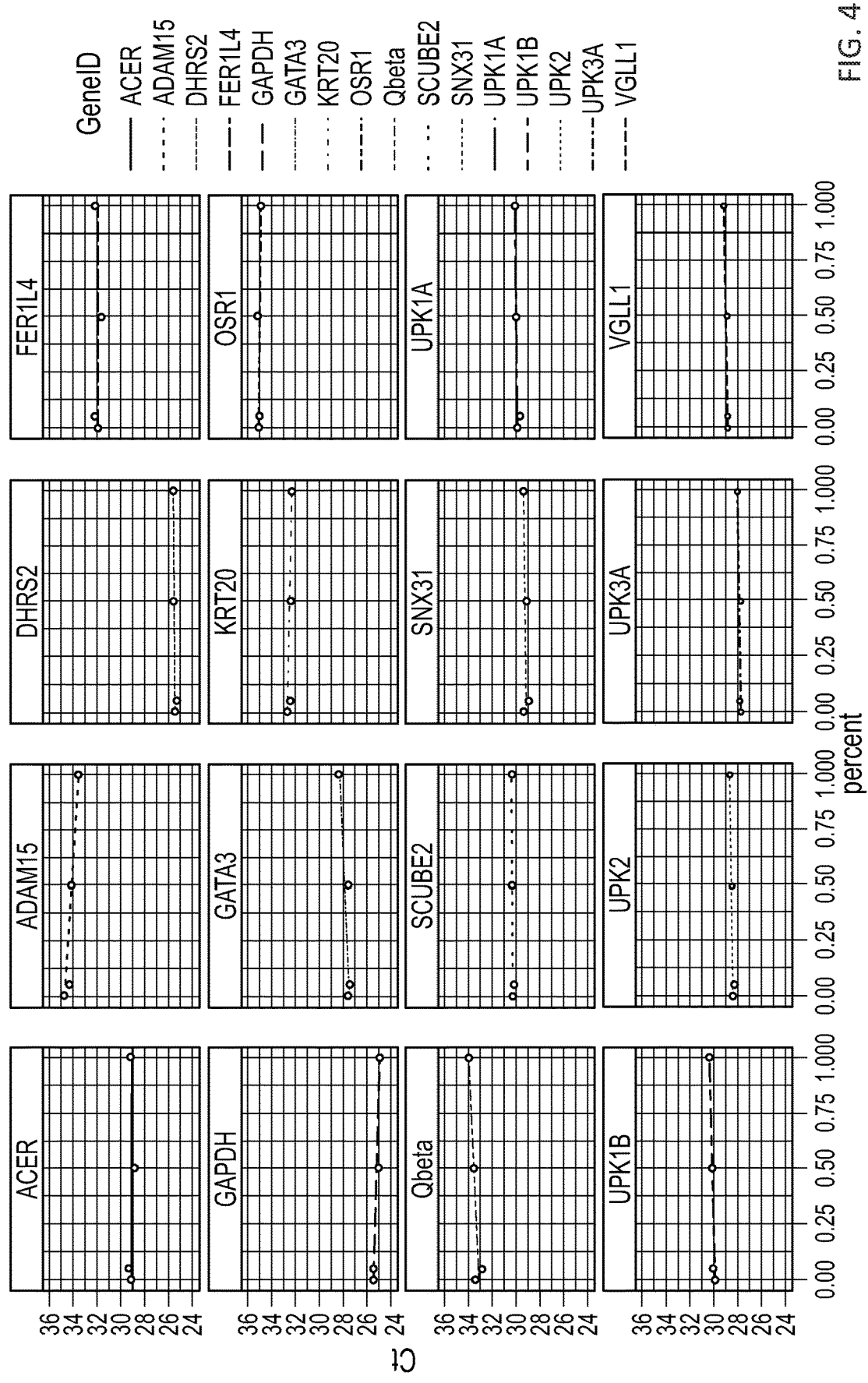
FIG. 4 is a series of graphs showing the expression levels (y-axis) of 15 biomarkers measured in urine samples containing varying amounts of blood (x-axis).
Figure 5:
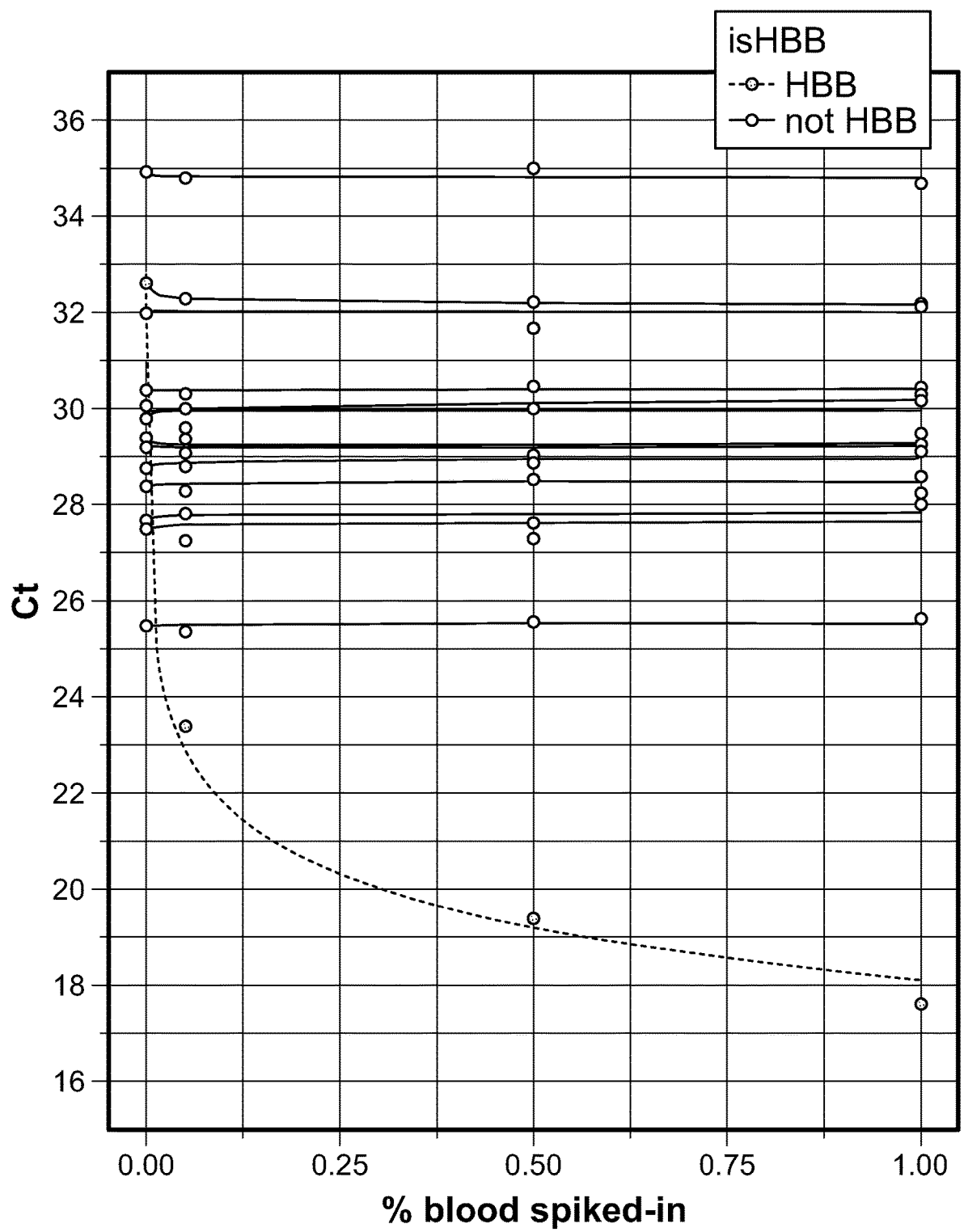
FIG. 5 is a graph showing the expression level (y-axis) of various biomarkers of the present disclosure and HBB measured in urine samples containing varying amounts of blood (x-axis).
Figure 6:
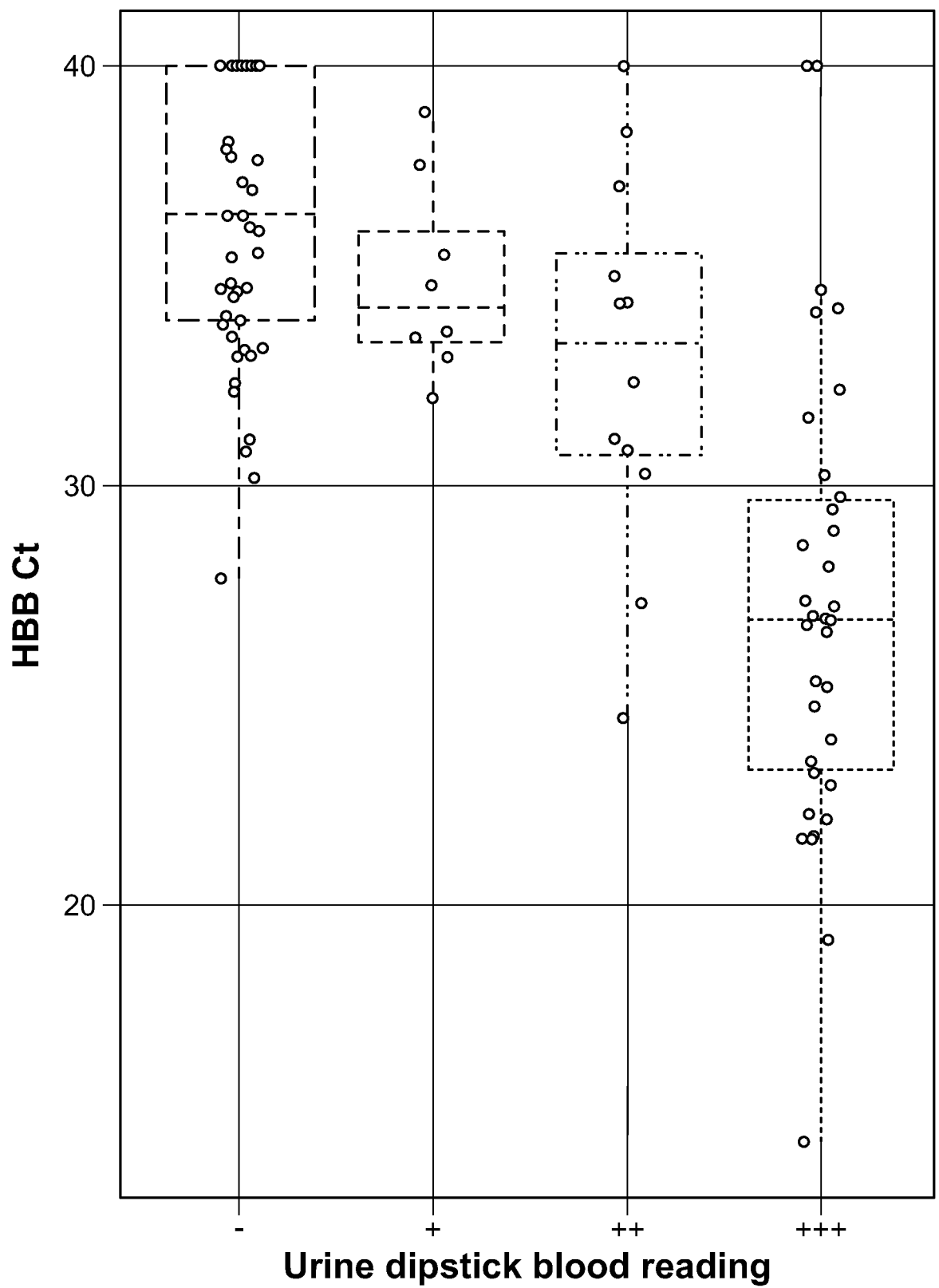
FIG. 6 is a graph showing the comparison of the measured expression level of HBB (y-axis) to the readout from a urine dipstick (x-axis).

A common symptom of bladder cancer is hematuria, or the presence of blood in urine. To determine whether the presence of blood in urine affected the measured expression levels of the candidate biomarkers DHRS2, UPK2, UPK1A, KRT20, UPK1B, ACER2, SNX31, VGLL1, FER1L4, UPK3A, OSR1, GATA3, SCUBE2, GAPDH, ADAM15, a urine sample was subdivided into four samples and spiked with blood to a final concentration of either 0%, 0.05% blood, 0.5% blood or 1% blood. Microvesicles from each sample were then isolated, the microvesicular RNA extracted and analyzed using qPCR. As shown in FIG. 4, the measured expression levels of each biomarker did not vary when the amount of blood in the urine sample was increased. As shown in FIG. 5, the expression level of HBB could be concurrently measured and correlated with the amount of blood that was added to each sample, while the measured expression levels of the biomarkers stayed constant. In fact, as shown in FIG. 6, the measured expression level of HBB correlated well with urine dipstick blood readings, indicating the methods of the present disclosure can be used to analyze a patient's urine sample for hematuria.

These results indicate that the methods of the present disclosure are robust with respect to the presence of blood in the urine samples used, which is in contrast to methods currently used in the art.

Example 3

The methods of the present disclosure yield reproducible and robust results. As shown in the left panel of FIG. 7, two independent operators analyzed the expression of 4 of the candidate biomarkers, GAPDH, CXCL10, UPK2 and DHRS2, as well as HBB, in microvesicles isolated from urine. The results of the two independent operators showed little variation, demonstrating the robustness of the methods of the present disclosure.

Figure 7:
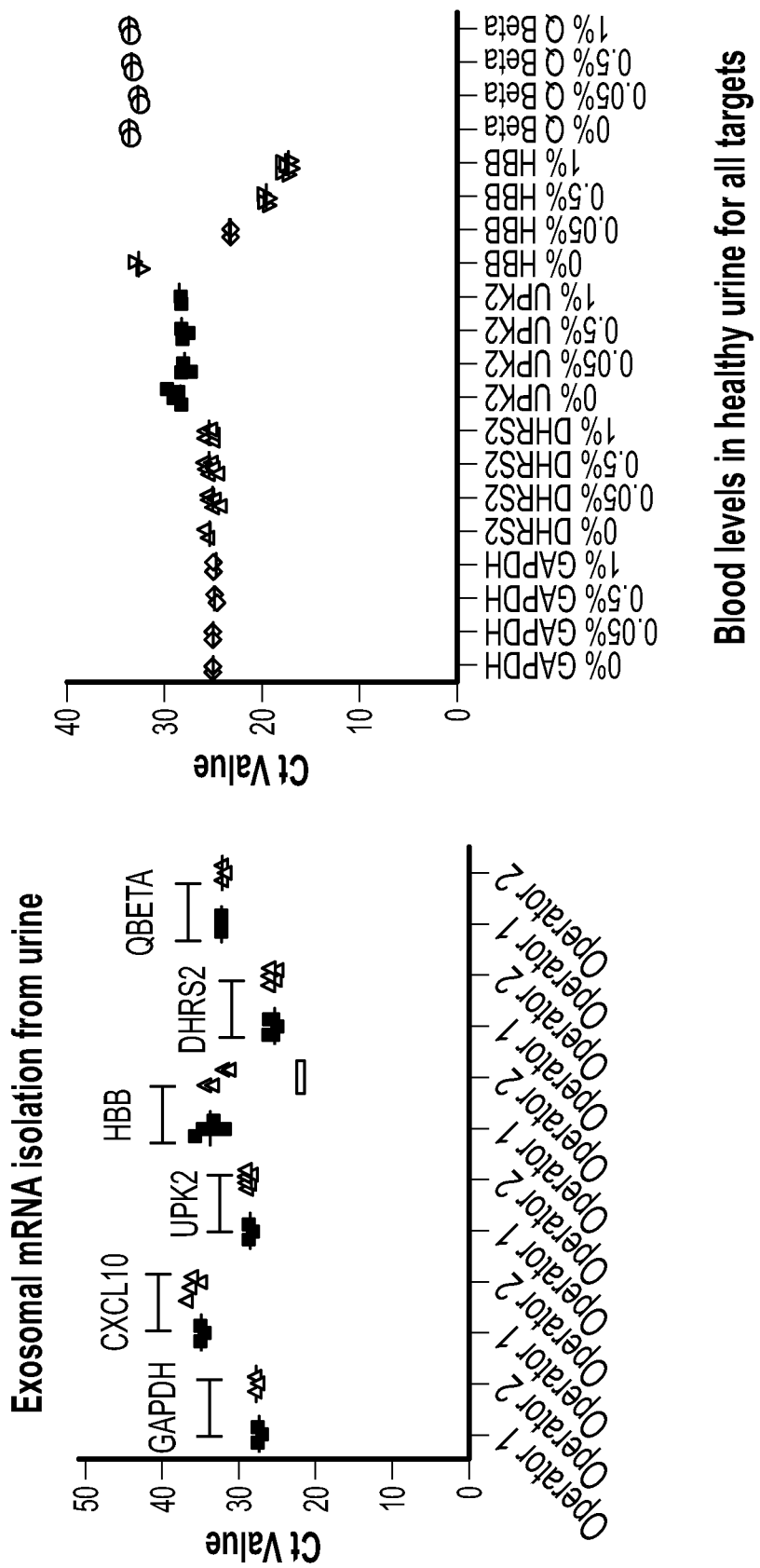
FIG. 7 is a series of graphs showing a comparison between the expression levels of various biomarkers of the present disclosure measured by two independent operators. The right panel shows the expression of biomarkers measured in urine samples that comprise varying amounts of blood.

Moreover, as shown in the right panel of FIG. 7 the two independent operators also analyzed the expression level of candidate biomarkers GAPDH, DHRS2 and UPK2, as well as HBB, in microvesicles isolated from urine samples spiked with blood. Again, the expression levels of the biomarkers measured between the two operators, as well as between the different blood levels, showed little variation, demonstrating the robustness of the methods of the present disclosure, particularly in regards to the presence of blood in the urine samples.

Example 4

Figure 8:
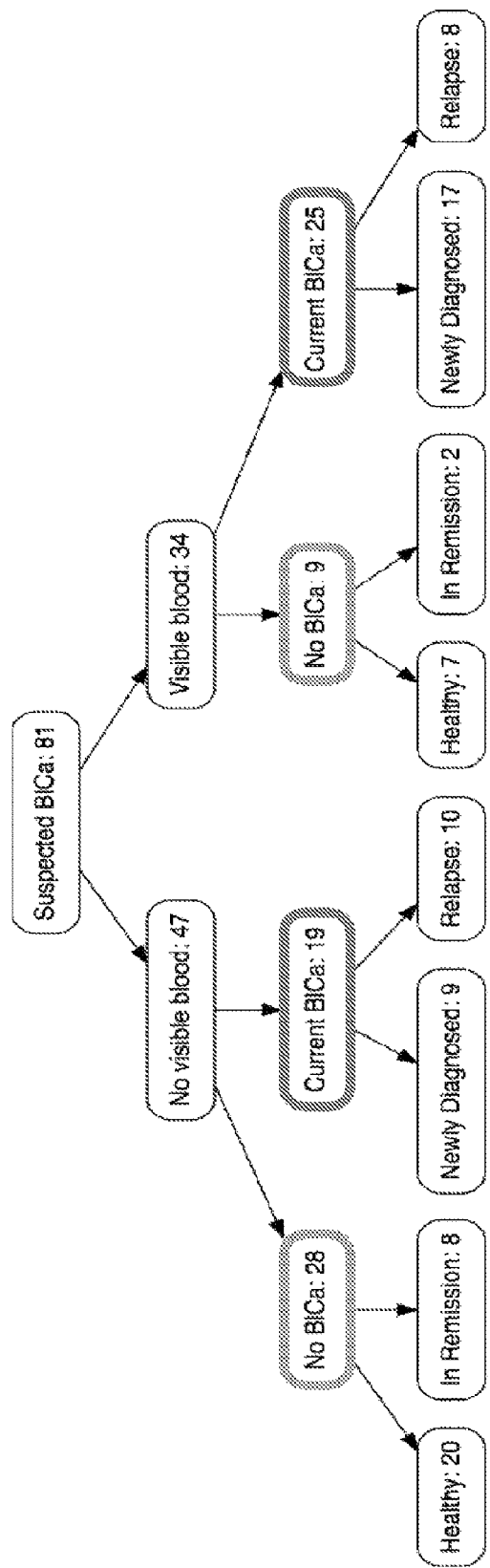
FIG. 8 is a flow chart showing the details of 81 clinical samples tested using the methods of the present disclosure.

Clinical urine samples from 81 subjects were collected. Of the 81 subjects, 44 of them were diagnosed with bladder cancer using standard methods, while the other 37 were suspected of having bladder cancer but were actually healthy (cancer free). As shown in FIG. 8, the clinical samples included urine samples with visible blood and without visible blood. Moreover, some of the samples were from subjects who were newly diagnosed, in remission or had relapsed.

Figure 9:
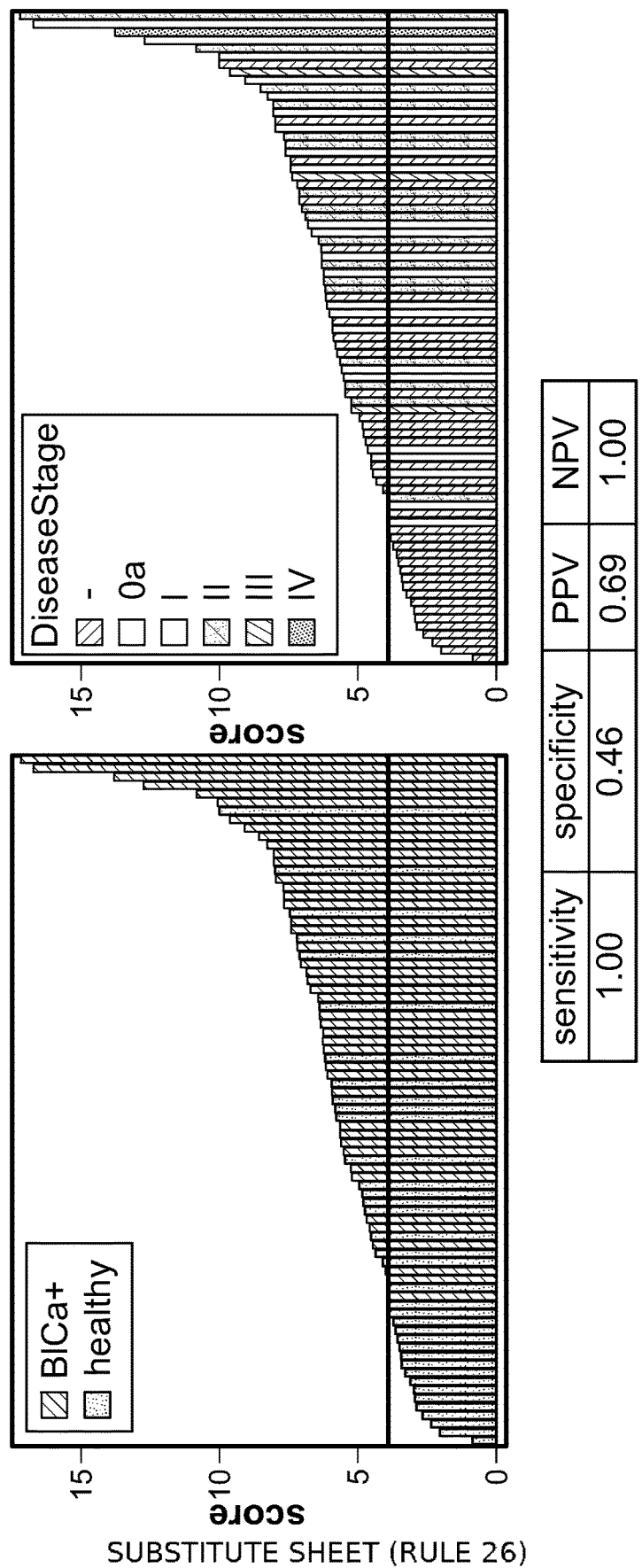
FIG. 9 is a series of charts showing the analysis of 81 clinical samples using the methods of the present disclosure, as described in example 4. In the left panel, bars are shaded according to whether the patient is healthy or has bladder cancer. In the right panel, the bars are shaded according to the severity of the disease. The thick, horizontal line on each graph is the cutoff score. Samples that are scored below the cutoff score are identified as healthy.

Microvesicles from each urine sample were isolated. The microvesicular nucleic acids were then extracted and the expression levels of UPK2, OSR1, KRT20 and DHRS2 were measured using qPCR. The expression levels of UPK2, OSR1 and KRT20 were normalized to DHRS2, which was used as a reference gene. A score was then generated by comparing the difference between the normalized expression level of OSR1 and the normalized expression level of UPK2 (OSR1 normalized expression minus UPK2 normalized expression) to a first predetermined cutoff value and the normalized expression level of KRT20 to a second predetermined cutoff value. A patient was deemed healthy if the difference between the normalized expression level of OSR1 and the normalized expression level of UPK2 was less than the first predetermined cutoff value and the normalized expression level of KRT20 was greater than the second predetermined cutoff value. As shown in FIG. 9, the method was able to rule out about 50% of healthy individuals, regardless of hematuria, whether the bladder cancer was new or relapsed/recurrent, or disease stage.

Example 5

Figure 10:
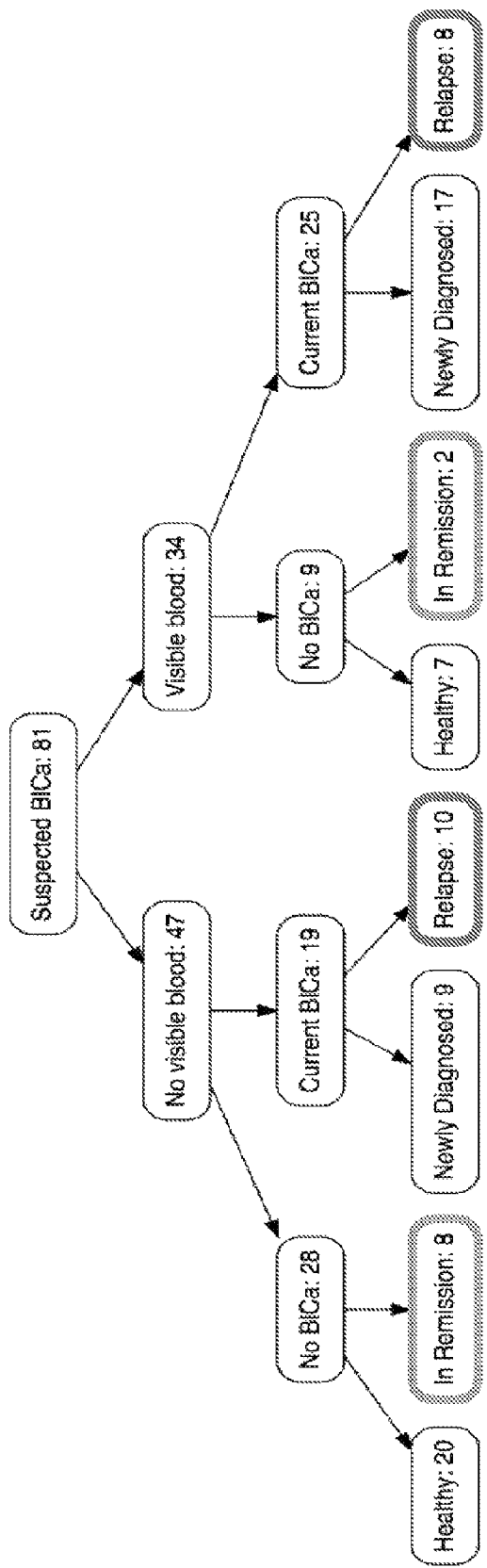
FIG. 10 is a flow chart showing the details of 81 clinical samples tested using the methods of the present disclosure. The 28 samples tested in example 5 are outlined in bold.

As shown in FIG. 10, of the 81 clinical samples from example 4, 18 of the samples were derived from subjects who had bladder cancer recurrence and 10 of the samples were derived from subjects who were suspected of having recurrent bladder cancer but were in fact healthy. These 28 samples were analyzed further using the methods of the present disclosure. As shown in FIG. 10, some of these the samples included urine samples with visible blood and without visible blood.

Figure 11:
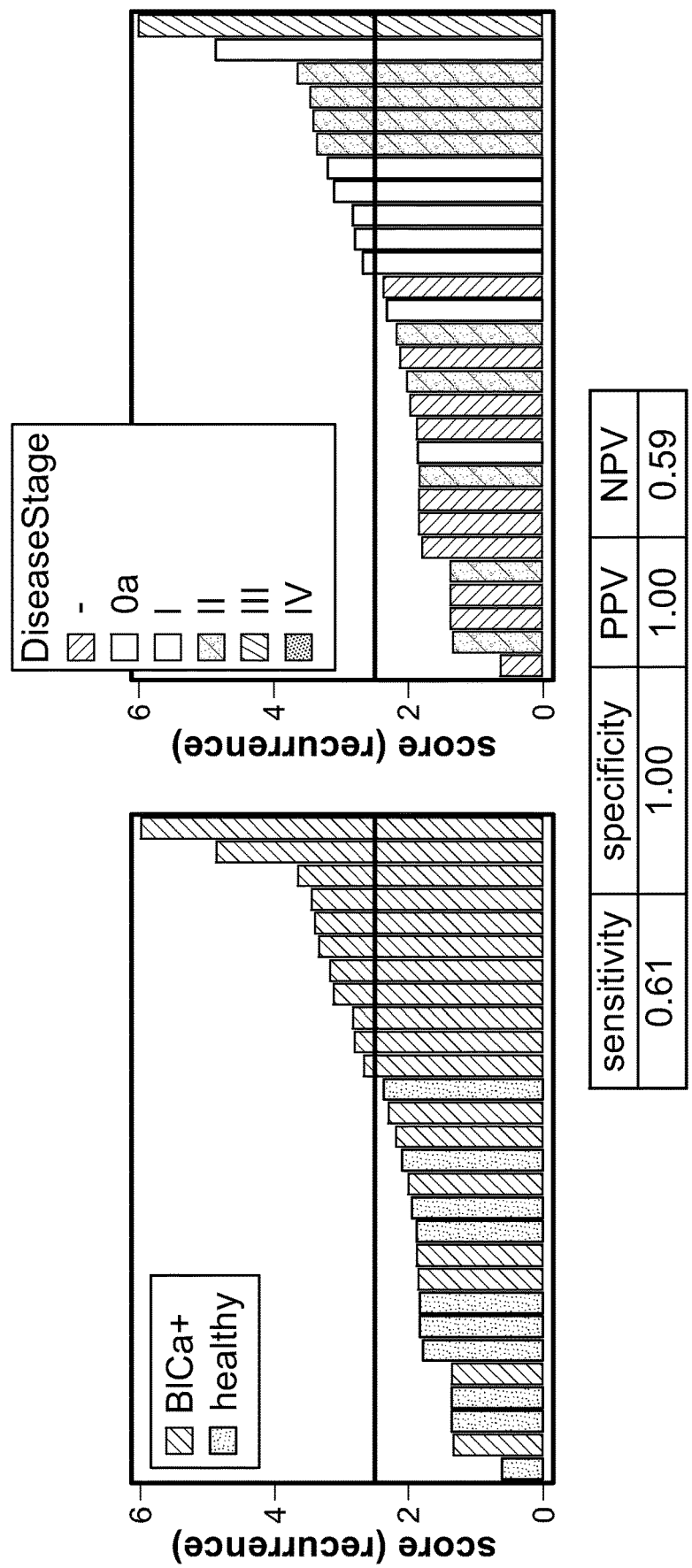
FIG. 11 is a series of charts showing the analysis of 28 clinical samples using the methods of the present disclosure, as described in Example 5. In the left panel, bars are shaded according to whether the patient is healthy or has bladder cancer. In the right panel, the bars are shaded according to the severity of the disease. The thick, horizontal line on each graph is the cutoff score. Samples that are scored above the cutoff score are identified as bladder cancer positive.

Microvesicles from the 28 samples were isolated. The microvesicular nucleic acids were then extracted and the expression levels of UPK2 and DHRS2 were measured using qPCR. The expression level of UPK2 was normalized to the expression level of DHRS2. A score was then generated by comparing the normalized UPK2 expression level to a predetermined cutoff value. A patient was deemed to have recurrent bladder cancer if the normalized UPK2 expression level was greater than the predetermined cutoff value. As shown in FIG. 11, the method was able to detect about 66% of recurrent tumors, regardless of hematuria or disease stage.

What is claimed is:
1. A method of treating bladder cancer in a human subject comprising:
   determining the expression levels of DHRS2 and UPK2 in microvesicular nucleic acid extracted from a urine sample from the human subject;
   normalizing the expression level of UPK2 to the expression level of DHRS2 to obtain a normalized expression level of UPK2;
   comparing the normalized expression level of UPK2 to a predetermined cutoff value; and
   administering to the human subject at least one therapeutically effective amount of at least one bladder cancer therapy when the normalized expression level of UPK2 is greater than the predetermined cutoff value.
2. A method of treating bladder cancer in a human subject comprising:
   determining the expression levels of DHRS2, UPK2, KRT20, and OSR1 in microvesicular nucleic acid extracted from a urine sample from the human subject;

normalizing the expression levels of UPK2, OSR1, and KRT20 to the expression level of DHRS2 to obtain normalized expression levels of UPK2, OSR1, and KRT20;

determining $\Delta_{expression}$, wherein $\Delta_{expression}$ is the difference between the normalized expression level of OSR1 and the normalized expression level of UPK2;

comparing $\Delta_{expression}$ to a first predetermined cutoff value;

comparing the normalized expression level of KRT20 to a second predetermined cutoff value; and administering to the human subject at least one therapeutically effective amount of at least one bladder cancer therapy when $\Delta_{expression}$ is greater than the first predetermined cutoff value and the normalized expression level of KRT20 is less than the second predetermined cutoff value.

3. The method of claim 2, wherein the bladder cancer is recurrent bladder cancer.

4. The method of claim 2, wherein the bladder cancer is relapsed bladder cancer.

5. The method of claim 2, wherein the microvesicular nucleic acid comprises microvesicular RNA.

6. The method of claim 2, wherein the urine sample is filtered or pre-processed to remove cells, cellular debris or any combination thereof.

7. The method of claim 2, wherein the microvesicular nucleic acid is extracted from at least one microvesicle isolated from the urine sample, wherein the at least one microvesicle is isolated by a method comprising filtration, size exclusion chromatography, ion exchange chromatography, density gradient centrifugation, centrifugation, differential centrifugation, immunoabsorbent capture, affinity purification, affinity enrichment, affinity exclusion microfluidic separation, ultracentrifugation, nanomembrane ultrafiltration or any combination thereof.

8. The method of claim 2, wherein the urine sample comprises at least 0.05% blood.

9. The method of claim 2, wherein the human subject has hematuria.

10. The method of claim 9, wherein the hematuria is gross hematuria or microscopic hematuria.

11. The method of claim 2, wherein the predetermined cutoff value has a positive predictive value of at least 50%.

12. The method of claim 2, wherein the predetermined cutoff value has a negative predictive value of at least 50%.

13. The method of claim 2, wherein the predetermined cutoff value has a sensitivity of at least 50%.

14. The method of claim 2, wherein the predetermined cutoff value has a specificity of at least 50%.

15. The method of claim 2, wherein the human subject is at least 40 years of age.

16. The method of claim 2, wherein the human subject previously had bladder cancer.

17. The method of claim 2, wherein the human subject previously had a radical cystectomy.

18. The method of claim 2, wherein the bladder cancer therapy comprises surgery, radiation therapy, chemotherapy, intravesical therapy, anti-cancer therapy, immunotherapy, intravesical immunotherapy, targeted-drug therapy, intravesical chemotherapy or any combination thereof.

19. The method of claim 2, wherein the expression levels are measured as a cycle threshold (Ct) value.

\* \* \* \* \*